(12) United States Patent
Smith

(10) Patent No.: US 6,942,671 B1
(45) Date of Patent: Sep. 13, 2005

(54) SURGICAL SEALING APPARATUS

(75) Inventor: Robert C. Smith, Hamden, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 609 days.

(21) Appl. No.: 09/706,643

(22) Filed: Nov. 6, 2000

(51) Int. Cl.⁷ .................................................. A61M 5/00
(52) U.S. Cl. ....................................................... 606/108
(58) Field of Search ........................... 606/108, 53, 130, 606/185

(56) References Cited

U.S. PATENT DOCUMENTS

| | | |
|---|---|---|
| 3,421,509 A | 1/1969 | Fiore |
| 3,565,078 A | 2/1971 | Vailliancourt et al. |
| 3,853,127 A | 12/1974 | Spademan |
| 3,907,310 A | 9/1975 | Dufour |
| 3,994,287 A | 11/1976 | Turp et al. |
| 4,000,739 A | 1/1977 | Stevens |
| 4,007,909 A | 2/1977 | Buseth et al. |
| 4,112,932 A | 9/1978 | Chiulli |
| 4,126,133 A | 11/1978 | Schwartz |
| 4,173,350 A | 11/1979 | Sieghartner |
| 4,177,814 A | 12/1979 | Knepshield et al. |
| 4,177,997 A | 12/1979 | Cartwright |
| 4,240,335 A | 12/1980 | Stucka et al. |
| 4,240,411 A | 12/1980 | Hosono |
| 4,311,315 A | 1/1982 | Kronenberg |
| 4,334,688 A | 6/1982 | Spargo et al. |
| 4,338,689 A | 7/1982 | Zieg |
| 4,386,756 A | 6/1983 | Muchow |
| 4,387,879 A | 6/1983 | Tauschinski |
| 4,430,081 A | 2/1984 | Timmermans |
| 4,447,237 A | 5/1984 | Frisch et al. |
| 4,464,178 A | 8/1984 | Dalton |
| 4,473,211 A | 9/1984 | Fremy |
| 4,553,760 A | 11/1985 | Reed et al. |
| 4,586,694 A | 5/1986 | Jones |
| 4,588,195 A | 5/1986 | Antonini et al. |
| 4,601,710 A | 7/1986 | Moll |
| 4,626,245 A | 12/1986 | Weinstein |
| 4,641,842 A | 2/1987 | Kataoka |
| 4,654,030 A | 3/1987 | Moll et al. |
| 4,655,752 A | 4/1987 | Honkanen et al. |
| 4,673,393 A | 6/1987 | Suzuki et al. |
| 4,686,977 A | 8/1987 | Cosma |
| 4,705,511 A | 11/1987 | Kocak |
| 4,715,360 A | 12/1987 | Akui et al. |
| 4,723,550 A | 2/1988 | Bales et al. |
| 4,758,225 A | 7/1988 | Cox et al. |
| 4,842,591 A | 6/1989 | Luther |
| 4,844,483 A | 7/1989 | Iijima et al. |
| 4,844,484 A | 7/1989 | Antonini et al. |
| 4,857,062 A | 8/1989 | Russell |

(Continued)

FOREIGN PATENT DOCUMENTS

| | | |
|---|---|---|
| DE | 3217118 | 8/1983 |
| EP | 0 029 864 | 6/1981 |
| EP | 0051718 | 5/1982 |
| EP | 0113520 | 7/1984 |
| EP | 0312219 | 4/1989 |
| EP | 0538060 | 9/1995 |
| GB | 1482857 | 8/1977 |
| GB | 2 298 905 | 9/1996 |
| WO | WO93/04717 | 3/1993 |
| WO | WO 94/07552 | 4/1994 |
| WO | WO 95/05207 | 2/1995 |
| WO | WO98/53865 | 12/1998 |

Primary Examiner—Ismael Izaguirre

(57) ABSTRACT

A sealing apparatus includes a housing mountable to an elongate shaft having an axial lumen and defining a pathway therein a. A sealing member defines a cavity and has at least a portion thereof disposed within the housing. The sealing member is adapted to traverse the pathway of the housing about an axis of curvature.

33 Claims, 12 Drawing Sheets

U.S. PATENT DOCUMENTS

| | | |
|---|---|---|
| 4,869,717 A | 9/1989 | Adair |
| 4,874,378 A | 10/1989 | Hillstead |
| 4,889,349 A | 12/1989 | Muller |
| 4,909,798 A | 3/1990 | Fleischhacker et al. |
| 4,917,668 A | 4/1990 | Haindl |
| 4,929,235 A | 5/1990 | Merry et al. |
| 4,932,633 A | 6/1990 | Johnson et al. |
| 4,943,280 A | 7/1990 | Lander |
| 4,960,412 A | 10/1990 | Fink |
| 4,966,588 A | 10/1990 | Rayman et al. |
| 4,998,740 A | 3/1991 | Tellier |
| 5,000,745 A | 3/1991 | Guest et al. |
| 5,002,557 A | 3/1991 | Hasson |
| 5,015,000 A | 5/1991 | Perini |
| 5,038,756 A | 8/1991 | Kepley |
| 5,041,095 A | 8/1991 | Littrell |
| 5,053,014 A | 10/1991 | Van Heugten |
| 5,053,016 A | 10/1991 | Lander |
| 5,073,169 A | 12/1991 | Raiken |
| 5,104,383 A | 4/1992 | Schicman |
| 5,123,164 A | 6/1992 | Shaheen et al. |
| 5,123,634 A | 6/1992 | Schwerdt |
| 5,127,626 A | 7/1992 | Hilal et al. |
| 5,137,520 A | 8/1992 | Maxson et al. |
| 5,167,636 A | 12/1992 | Clement |
| 5,180,373 A | 1/1993 | Green et al. |
| 5,197,955 A | 3/1993 | Stephens et al. |
| 5,201,714 A | 4/1993 | Gentelia et al. |
| 5,209,736 A | 5/1993 | Stephens et al. |
| 5,209,737 A | 5/1993 | Ritchart et al. |
| 5,211,633 A | 5/1993 | Stouder, Jr. |
| 5,221,264 A | 6/1993 | Wilk et al. |
| 5,224,930 A | 7/1993 | Spaeth et al. |
| 5,226,891 A | 7/1993 | Bushatz et al. |
| 5,242,412 A | 9/1993 | Blake, III |
| 5,251,873 A | 10/1993 | Atkinson et al. |
| 5,273,545 A | 12/1993 | Hunt et al. |
| 5,290,304 A | 3/1994 | Storace |
| 5,295,657 A | 3/1994 | Atkinson |
| 5,299,813 A | 4/1994 | McKenna |
| 5,300,033 A | 4/1994 | Miller |
| 5,300,035 A | 4/1994 | Clement |
| 5,300,036 A | 4/1994 | Mueller et al. |
| 5,308,336 A | 5/1994 | Hart et al. |
| 5,330,436 A | 7/1994 | Heidmueller |
| 5,334,164 A | 8/1994 | Guy et al. |
| 5,338,307 A | 8/1994 | Stephens et al. |
| 5,342,315 A | 8/1994 | Rowe et al. |
| 5,350,362 A | 9/1994 | Stouder, Jr. |
| 5,366,446 A | 11/1994 | Tal et al. |
| 5,380,288 A | 1/1995 | Hart et al. |
| 5,385,553 A | 1/1995 | Hart et al. |
| 5,389,080 A | 2/1995 | Yoon |
| 5,389,081 A | 2/1995 | Castro |
| 5,391,153 A | 2/1995 | Haber et al. |
| 5,395,342 A | 3/1995 | Yoon |
| 5,397,335 A | 3/1995 | Gresl et al. |
| 5,403,284 A | 4/1995 | Gross |
| 5,405,330 A | 4/1995 | Zunitch et al. |
| 5,407,433 A | 4/1995 | Loomas |
| 5,411,483 A | 5/1995 | Loomas et al. |
| 5,423,761 A | 6/1995 | Hein et al. |
| 5,460,616 A | 10/1995 | Weinstein et al. |
| 5,476,475 A | 12/1995 | Gadberry |
| 5,478,318 A | 12/1995 | Yoon |
| 5,492,304 A | 2/1996 | Smith et al. |
| 5,496,280 A | 3/1996 | Vandenbroek et al. |
| 5,509,643 A | 4/1996 | Carstens et al. |
| 5,512,053 A | 4/1996 | Pearson et al. |
| 5,514,133 A | 5/1996 | Golub et al. |
| 5,531,758 A | 7/1996 | Uschold et al. |
| 5,540,661 A | 7/1996 | Tomisaka et al. |
| 5,545,142 A | 8/1996 | Stephens et al. |
| 5,554,124 A | 9/1996 | Alvarado |
| 5,569,205 A | 10/1996 | Hart et al. |
| 5,584,850 A | 12/1996 | Hart et al. |
| 5,603,702 A | 2/1997 | Smith et al. |
| 5,607,397 A | 3/1997 | Stephens et al. |
| 5,613,663 A | 3/1997 | Schmidt et al. |
| 5,628,732 A | 5/1997 | Antoon, Jr. et al. |
| 5,634,908 A | 6/1997 | Loomas |
| 5,657,963 A | 8/1997 | Hinchliffe et al. |
| 5,662,615 A | 9/1997 | Blake, III |
| 5,676,657 A | 10/1997 | Yoon |
| 5,685,854 A | 11/1997 | Green et al. |
| 5,709,664 A | 1/1998 | Vandenbroek et al. |
| 5,720,759 A | 2/1998 | Green et al. |
| 5,752,938 A | 5/1998 | Flatland et al. |
| 5,755,702 A | 5/1998 | Hillstead et al. |
| 5,779,697 A | 7/1998 | Glowa et al. |
| 5,782,817 A | 7/1998 | Franzel et al. |
| 5,792,113 A | 8/1998 | Kramer et al. |
| 5,820,600 A | 10/1998 | Carlson et al. |
| 5,820,604 A | 10/1998 | Fox et al. |
| 5,820,606 A | 10/1998 | Davis et al. |
| 5,827,228 A | 10/1998 | Rowe |
| 5,839,639 A | 11/1998 | Sauer et al. |
| 5,865,817 A | 2/1999 | Moenning et al. |
| 5,868,714 A | 2/1999 | Danks |
| 5,871,471 A | 2/1999 | Ryan et al. |
| 5,906,595 A | 5/1999 | Powell et al. |
| 5,989,224 A | 11/1999 | Exline et al. |
| 5,993,471 A | 11/1999 | Riza et al. |
| 6,000,670 A | 12/1999 | Okamoto |
| 6,030,403 A | 2/2000 | Long et al. |
| 6,039,725 A * | 3/2000 | Moenning et al. .......... 604/108 |
| RE36,702 E | 5/2000 | Green et al. |
| 6,066,117 A | 5/2000 | Fox et al. |
| 6,068,011 A | 5/2000 | Paradis |
| 6,077,249 A | 6/2000 | Dittrich et al. |
| 6,077,288 A | 6/2000 | Shimomura et al. |
| 6,083,203 A | 7/2000 | Yoon |
| 6,093,176 A | 7/2000 | Dennis |
| 6,110,154 A | 8/2000 | Shimomura et al. |
| 6,123,689 A | 9/2000 | To et al. |
| 6,159,182 A | 12/2000 | Davis et al. |
| 6,176,843 B1 | 1/2001 | DiCaprio et al. |
| 6,197,002 B1 | 3/2001 | Peterson |
| 6,217,555 B1 | 4/2001 | Hart et al. |
| 6,231,565 B1 | 5/2001 | Tovey et al. |

* cited by examiner

SURGICAL SEALING APPARATUS

BACKGROUND

1. Technical Field

The present disclosure relates generally to a sealing apparatus and methods that facilitate percutaneous access of surgical instruments into a patient's body, and more particularly, to a sealing apparatus that movably accommodates instrumentation while maintaining a gas and/or fluid tight seal therewith.

2. Background of Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example, in surgical procedures having the surgical region insufflated. For such procedures, the introduction of a tube into certain anatomical cavities, such as the abdominal cavity, is usually accomplished by use of a system incorporating a trocar and cannula assembly. Since the cannula is in direct communication with the internal portion of the seal assembly, insertion of the cannula into an opening in the patient's body to reach the inner abdominal cavity should be adapted to maintain a fluid tight interface between the abdominal cavity and the outside atmosphere. In view of the need to maintain the atmospheric integrity of the inner area of the cavity, a seal assembly for a cannula which permits introduction of a wide range of surgical instrumentation and maintains the atmospheric integrity of the inner area of the cavity is desirable. In this regard, there have been a number of attempts in the prior art to provide such sealing requirements. A difficulty encountered is the capability of accommodating the wide range of instrumentation and the angle and orientation from which the instrumentation is introduced and ultimately used.

SUMMARY

Accordingly, the present disclosure provides a sealing apparatus capable of accommodating various instrumentation for introduction into a body cavity with the ability to accommodate such instrumentation at various orientations. Moreover, the present disclosure accommodates such instrumentation while maintaining a substantially fluid tight seal about the instrumentation during introduction and manipulation of the instrumentation with the body cavity.

The present disclosure features a sealing apparatus having relatively moveable components that facilitate lateral and vertical movement of an instrument engaging cavity of the sealing apparatus relative to a stationary elongate shaft, such as, for example, a cannula.

BRIEF DESCRIPTION OF THE DRAWINGS:

Various embodiments are described hereinbelow with reference to the drawings wherein.

DETAILED DESCRIPTION OF EXEMPLARY EMBODIMENTS

In the following description, as is traditional, the term "proximal" refers to the portion of the instrument closest to the operator while the term "distal" refers to the portion of the instrument remote from the operator.

Figure 1:
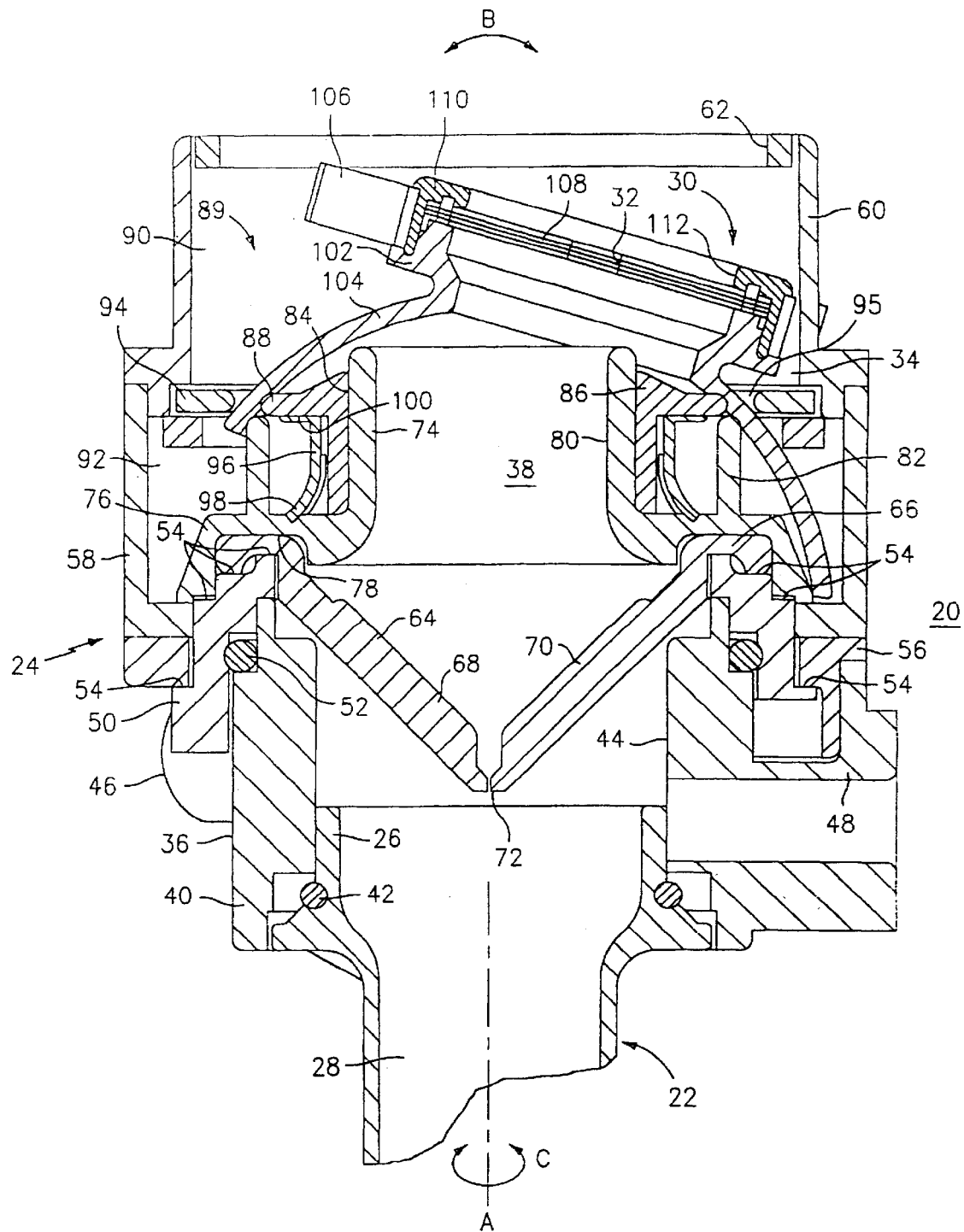
FIG. 1 is a side cross-sectional view of one embodiment of a sealing apparatus, shown in cut-away, in accordance with the principles of the present disclosure.
Figure 2:
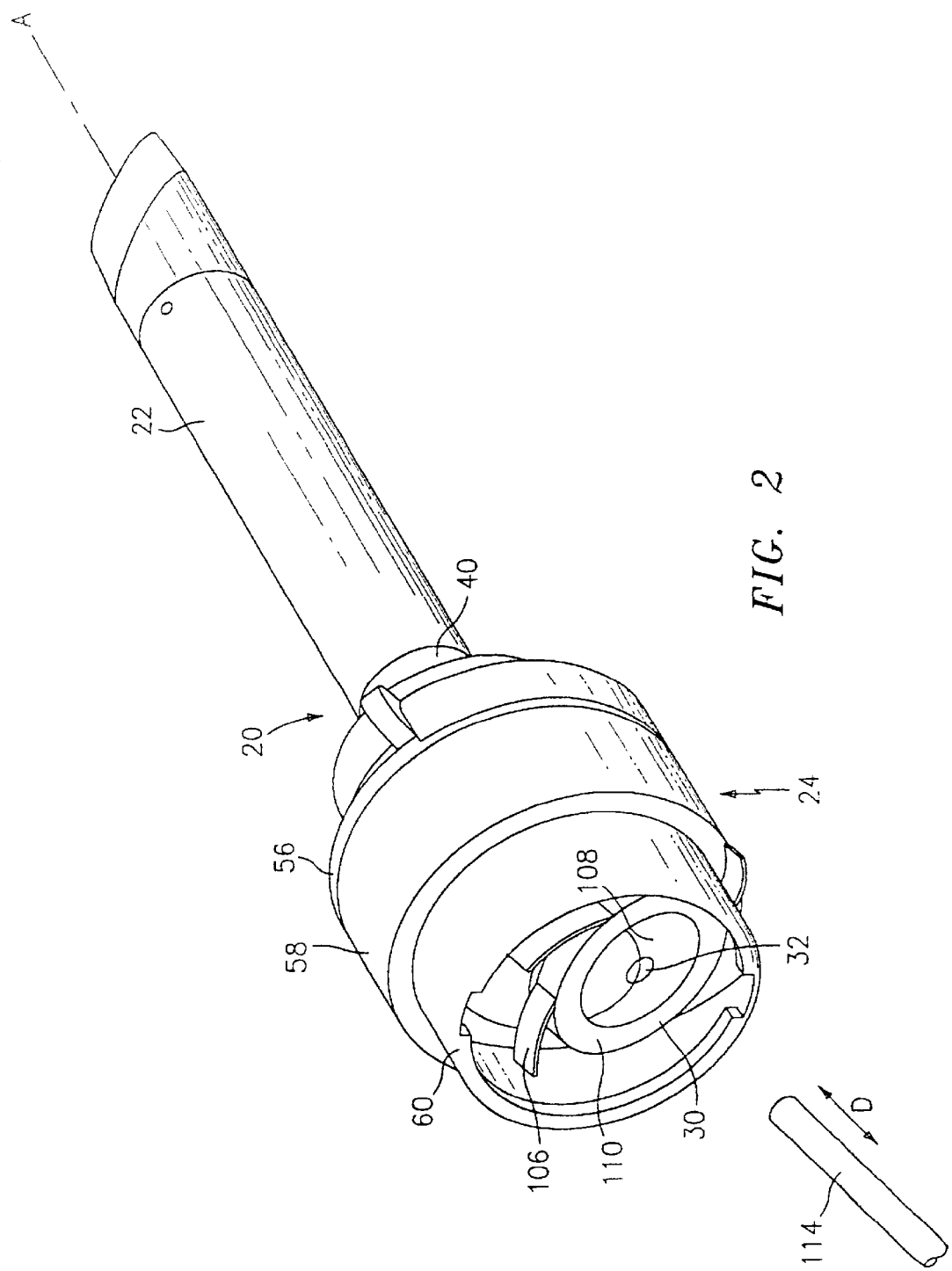
FIG. 2 is a perspective view of the sealing apparatus shown in FIG. 1 with an instrument to be introduced.

Referring initially to FIGS. 1 and 2, there is illustrated a sealing apparatus 20 constructed in accordance with the principles of the present disclosure which includes an elongate shaft, such as, for example, a cannula 22 of a cannula assembly. Sealing apparatus 20 contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. This feature of the present disclosure advantageously ensures that gases and/or fluids do not enter or exit a body cavity. Examples of such instrumentation include clip appliers, graspers, dissectors, retractors, staplers, laser probes, photographic devices, endoscopes and laparoscopes, tubes, and the like. Such instruments will be collectively referred to herein as "instruments and/or instrumentation".

Sealing apparatus 20 is useful for introducing instrumentation through percutaneous penetrations into a variety of target locations within a patient's body for a variety of purposes. Such purposes include drainage, intra-organ drug administration, feeding, perfusion, aspiration, and the like, most usually being the introduction of view scopes and surgical instruments for use in minimally invasive procedures, such as, laparoscopy, thorascopy, arthroscopy and the like.

Sealing apparatus 20 will typically be used in conjunction with, for example, a trocar or a radial expandable introducer for providing percutaneous access to an internal operative site during a surgical procedure. Usually, the trocar includes an obturator which is initially present in the cannula and facilitates penetration of cannula 22 through the patient's skin. After penetrating the patient's skin, the obturator is removed to provide a port for access into a body cavity. The length of cannula 22 will vary depending on the intended usage, but will generally be in the range of 5 centimeters to 25 centimeters. Sealing apparatus 20 includes a housing 24 which is mounted to a cannula housing 40, discussed below, that is attached to a proximal end 26 of cannula 22. Cannula 22 includes an axial lumen 28 and defines a longitudinal axis A. The components of sealing apparatus 20 have a substantially circular configuration. It is contemplated that the components may have other geometric shapes and sizes, such as, for example, rectangular, elliptical, etc., according to the surgical application and/or preference of a user.

It is contemplated that sealing apparatus 20 is detachably mountable to proximal end 26 of cannula 22. Thus, the surgeon can remove components of sealing apparatus 20 from cannula 22 at any time during the surgical procedure and, similarly, mount sealing apparatus 20 to cannula 22 when desired to provide a sealing engagement with instrumentation to be inserted through cannula 22. In addition, sealing apparatus 20 may be readily adapted for mounting to conventional cannulas of different structures. The detachability of sealing apparatus 20 from cannula 22 facilitates specimen removal through cannula 22 and reduces the profile of cannula 22 when sealing apparatus 20 is not needed for the surgical procedure.

Sealing apparatus 20 has a sealing member 30 that is moveably disposed within housing 24 and defines a cavity 32 configured for receipt of a surgical instrument 114. Movement of sealing member 30 causes spherical movement of cavity 32 relative to cannula 22, as will be discussed in greater detail hereinbelow. Sealing apparatus 20 has relatively moveable components that provide the spherical movement referred to facilitating lateral and vertical movement of cavity 32 relative to cannula 22. This feature advantageously facilitates accommodation of various instrumentation for introduction into a body cavity at various angles and orientations. Moreover, the disclosed configuration accommodates instrument 114 while maintaining a fluid tight seal (fluid tight includes preventing leakage of gases and/or fluids) about the outer surface of instrument 114 during introduction and manipulation with the body cavity.

Housing 24 includes a proximal portion 34, a distal portion 36 and a passageway 38 that are in fluid communication with axial lumen 28 of cannula 22. Housing 24 is integrally assembled of its constituent components from a rigid material suitable for surgical applications, such as, for example, a polymeric material or stainless steel, depending on the particular surgical application and/or preference of a user. It is contemplated that housing 24 may be monolithically formed. Housing 24 may be die cast from suitable metals or molded from suitable plastics. One skilled in the art, however, will realize that other materials and fabrication methods suitable for assembly and manufacture, in accordance with the present disclosure, also would be appropriate.

A cannula housing 40 is detachably mounted to proximal end 26 of cannula 22. Cannula housing 40 is mounted to cannula 22 forming a substantially fluid tight seal therewith. It is envisioned that cannula housing 40 may be readily adapted for mounting to conventional cannulas of different structures. It is contemplated that cannula housing 40 may be fixedly mounted to cannula 22 and the remaining components of sealing apparatus 20 being detachable therefrom.

A gasket 42 facilitates sealing engagement of cannula housing 40 with cannula 22. Cannula housing 40 has a generally circular cross-section and defines a longitudinal opening 44 which forms a portion of passageway 38. Longitudinal opening 44 is configured for reception and passage of surgical instrument 114. Cannula housing 40 has an exterior surface 46 that is engageable by a user for manipulation of sealing apparatus 20. The user may manipulate exterior surface 46 of cannula housing 40 for mounting on to cannula 22. It is contemplated that cannula housing 40 may be friction fit, threaded, etc., to cannula 22.

Cannula housing 40 includes a stopcock valve or port 48 that permits passage of insufflation gases through cannula 22 and into the body cavity (not shown). Stopcock valve 48 extends radially outward from cannula housing 40. Stopcock valve 48 is configured for communication with passage 38 during insufflation and may also be used for irrigating, aspirating and the like.

A stabilizing plate 50 is mounted to cannula housing 40 in a sealing engagement. A gasket 52 facilitates sealing engagement of stabilizing plate 50 with cannula housing 40 thereby forming a substantial seal between the body cavity of a patient and the outside atmosphere. Stabilizing plate 50 includes stepped portions 54 that provide support and alignment of various components of sealing apparatus 20, as will be discussed below. Stabilizing plate 50 may be fabricated from a rigid material, such as, for example, stainless steel or a polymeric material, similar to that discussed above.

An annular ring 56 is abutted against a lower retainer 58 of housing 24 and both are mounted to stabilizing plate 50 for support and enclosure of the internal components of sealing apparatus 20. Annular ring 56 is mounted to a stepped portion 54 of stabilizing plate 50. Lower retainer 58 is mounted to annular ring 56 and engages stabilizing plate 50. Annular ring 56 and lower retainer 58 have a substantially circular cross-section.

An upper retainer 60 of housing 24 is mounted to lower retainer 58 for support and enclosure of internal components of sealing apparatus 20. Upper retainer 60 includes an opening 62 in communication with passageway 38 and configured for reception and passage of surgical instrument 114. Upper retainer 60, lower retainer 58 and annular ring 56 may be appropriately mounted together by threading, adhesives, bayonet locking, etc., as readily understood by one skilled in the art.

A sealing valve 64 is disposed within passageway 38 of housing 24. Sealing valve 64 includes a flange portion 66 that is supported on step portion 54 of stabilizing plate 50. Sealing valve 64 is a conical elastomeric membrane, such as a duckbill valve, fabricated from a resilient material, such as, for example, rubber, etc. Sealing valve 64 is flexible for resilient reception of surgical instrumentation and maintaining seal integrity between the body cavity and the outside atmosphere. Sealing valve 64 includes a first member 68 and a second member 70 that are inwardly biased to a contact region 72 so as to form a substantial seal. First and second members 68,70 define contact region 72 which is configured for receiving instrument 114. It is contemplated that sealing valve 64 may include multiple members for abutting at contact region 72.

Contact region 72 permits passage of instrumentation through sealing valve 64 whereby first member 68 and second member 70 form a substantial seal with instrument 114 when inserted therethrough. In the absence of instrumentation disposed within sealing apparatus 20, and particularly when cannula 22 is inserted into an insufflated body cavity, contact region 72 forms a fluid tight seal that isolates the insufflated cavity from the outside atmosphere. It is contemplated that other conventional valves may be used for this purpose, such as, for example, a septum valve having a pre-formed puncture or crossed-slits for receiving instrument 114.

A support tower 74 is disposed within housing 24 and configured for alignment and support of components of sealing apparatus 20. Support tower 74 includes a flange portion 76 defining a recessed portion 78 for mounting to sealing valve 64. Flange portion 76 engages stabilizing plate 50 and lower retainer 58 for support and alignment thereof. Support tower 74 defines an opening 80 in communication with passageway 38 and configured for reception and passage of surgical instrument 114.

Support tower 74 has a substantially circular cross-section and is fabricated from polymerics, stainless steel, etc., similar to that described above. Support tower 74 includes a band 82 configured for support and definition of the moveable pathway of sealing member 30, as will be discussed below. An outer surface 84 of support tower 74 is configured for supporting engagement of a sealing element 86.

Sealing element 86 is mounted to outer surface 84 by threading, adhesives, etc., facilitating support and definition of the moveable pathway of sealing member 30. Sealing element 86 has a substantially circular cross-section or donut-like shape and is fabricated from an elastomeric material such as, for example, rubber, etc. Sealing member 30 is movably supported on a flange 88 of sealing element 86 and forms a substantial seal therewith. An annular ring 94 engages upper retainer 60 and in cooperation with lower retainer 58 facilitates support and alignment of upper retainer 60 of housing 24. Annular ring 94 includes a base portion 96 which engages sealing element 86 and a flared portion 98 that engages support tower 74. Base portion 96 includes a flange portion 100 which engages flange 88 of sealing element 86 for support and alignment of sealing element 86 within housing 24.

Annular ring 94 facilitates alignment of support tower 74 and sealing element 86 to define a moveable pathway 89 of sealing member 30. Sealing element 86, support tower 74, an inner surface of lower retainer 58, an inner surface of upper retainer 60 and annular ring 94 cooperate to define pathway 89. Pathway 89 includes a first portion, such as, for example, an upper portion 90 and a second portion, such as, for example, a lower portion 92. Upper portion 90 and lower portion 92 are separated by annular ring 94. An opening 95 formed radially about annular ring 94 permits movement of sealing member 30, as will be discussed, and facilitates communication of upper portion 90 with lower portion 92.

Sealing member 30 has a substantially parabolic cross-section and includes an end portion, such as, for example, a collar 102 and a bell portion 104. Bell portion 104 of sealing member 30 is spherically moveable within upper portion 90 and lower portion 92 as facilitated by movement through opening 95 of annular ring 94. Spherical movement of bell portion 104 includes a combination of arcuate movement relative to cannula 22, in the direction shown by arrows B, and rotatable movement about longitudinal axis A, in the direction shown by arrows C. The spherical movement described is advantageously facilitated by pathway 89 defined by the constituent parts of sealing apparatus 20, discussed above.

Collar 102 is spherically moveable within upper portion 90. Spherical movement of collar 102 defines the moveable bounds of sealing member 30 as limited by the interior surface of upper retainer 60 and annular ring 94. It is contemplated that engagement of surgical instrument 114 with housing 24 and/or the cannula assembly, when disposed with sealing member 30, may also moveably limit sealing member 30. Collar 102 and bell portion 104 are integrally assembled and fabricated using polymeric materials, stainless steel, etc., similar to that discussed above. It is contemplated that collar 102 and bell portion 104 may be monolithically formed.

Sealing member 30 includes biasing members 106 configured to engage the inner surface of upper retainer 60. Biasing members 106 are mounted to sealing member 30 with a cap ring, discussed below, and fabricated from a resilient material configured to bias sealing member 30 to a centered position relative to longitudinal axis A.

Sealing member 30 includes flexible seal 108. Flexible seal 108 is a thin annular elastomeric membrane that defines cavity 32 which is configured to receive surgical instrument 114. It is envisioned that flexible seal 108 may have other geometric configurations, such as, for example, rectangular, oval, etc. Flexible seal 108 may be fabricated from flexible materials suitable for surgical applications, such as, for example, silicone, rubber, urethane, etc. Flexible seal 108 is positioned with sealing member 30 such that cavity 32 is spherically moveable relative to cannula 22. Flexible seal 108 defines cavity 32 that is aligned with opening 62 of upper retainer 60, passageway 38 and axial lumen 28 of cannula 22.

Cavity 32 is configured for receiving substantially cylindrical instruments. Cavity 32 has a circular configuration to minimize gas and/or fluid leakage through flexible membrane 108. It is contemplated that cavity 32 may have other geometric configurations, such as, for example, elliptical, rectangular, etc., according to the configuration of the surgical instruments. Cavity 32 may, for example, have an inner diameter ranging from 0.1 mm to 3 mm which is consequently less than the outer diameter of the surgical instruments passing therethrough. Surgical instrument diameters may, for example, range from 5 mm to 12 mm.

Flexible seal 108 is sufficiently resilient to accommodate and provide a fluid tight seal with instruments of varying diameters. The tip of surgical instrument 114 is caused to engage and pass through cavity 32 stretching flexible seal 108 distally while also permitting relatively easy passage of surgical instrument 114 through sealing apparatus 20. Flexible seal 108 engages surgical instrument 114 to form a substantially fluid tight seal about surgical instrument 114 as it passes therethrough. Surgical instrument 114 is further advanced through sealing apparatus 20 to sealing valve 64 whereby contact region 72 forms a substantial seal with instrument 114.

Flexible seal 108 is retained within sealing member 30 by a cap ring 110. Cap ring 110 cooperates with collar 102 for aligning and retaining biasing members 106 with sealing member 30. Cap ring 110 includes an opening 112 for receipt and passage therethrough of surgical instrument 114. Cap ring 110 may be fabricated from a polymeric material, stainless steel, etc., similar to that discussed above.

Figure 3:
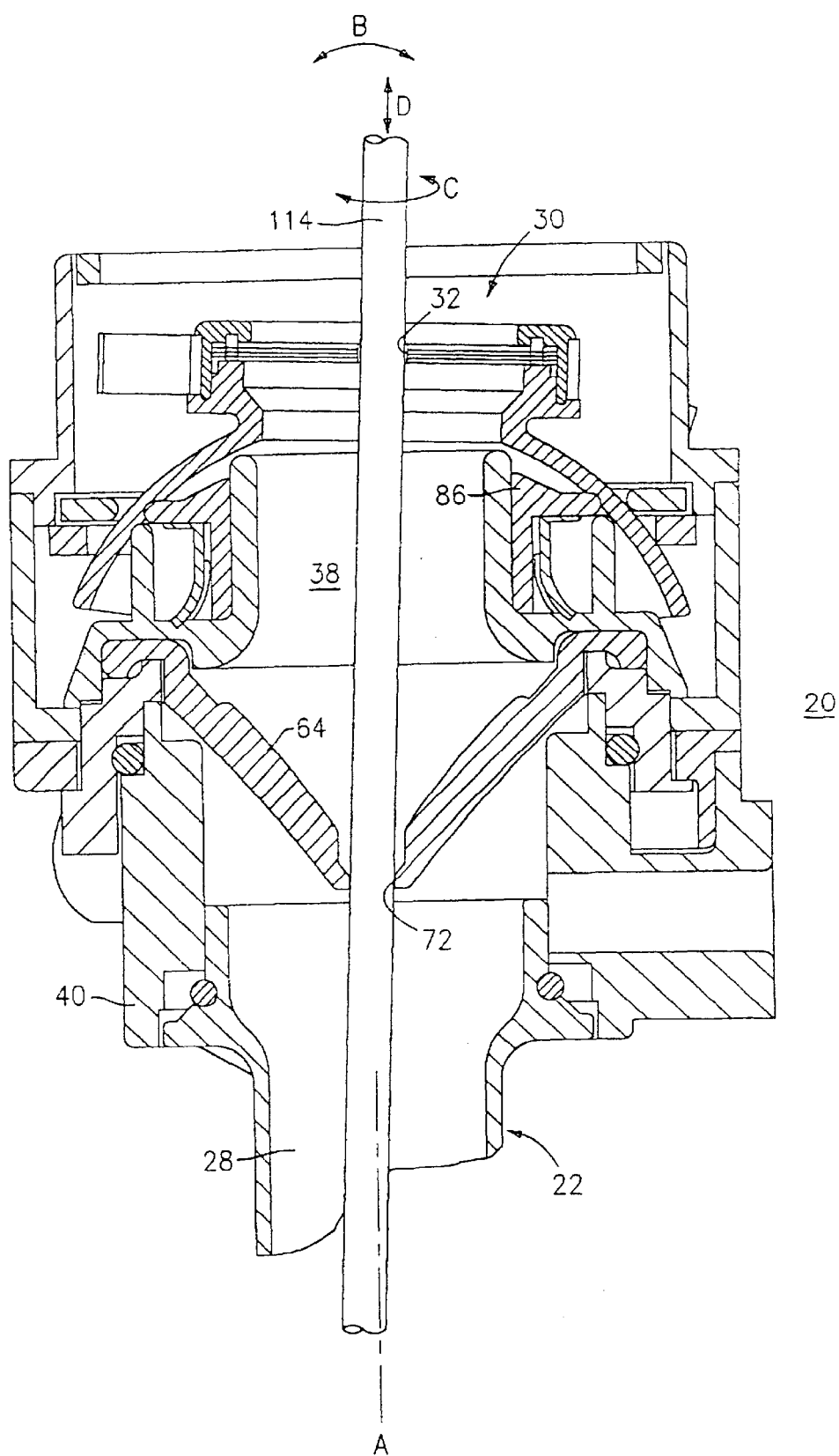
FIG. 3 is a side cross-sectional view, shown in cut-away, of the sealing apparatus shown in FIG. 1 with an instrument disposed therein.

Referring to FIGS. 2 and 3, in operation, sealing apparatus 20 accommodates movement and maintains a substantial seal with various surgical instruments during a surgical procedure. Prior to introducing surgical instrument 114 or a viewing scope, an obturator, insufflation needle or similar access device will be used to create a percutaneous penetration in the patient and to withdraw or introduce fluids into the body cavity. A trocar having an obturator is extended beyond cannula 22 and placed against the skin at the body cavity region and pressure exerted. This pressure causes the obturator to enter the skin and underlying tissue. Once the tip has penetrated the tissue and has entered the cavity, the tip automatically retracts into cannula 22 (See, for example, U.S. Pat. No. 5,116,353) and the trocar can be withdrawn from cannula 22 to permit introduction of surgical instrument 114. Alternatively, the trocar may have a spring biasing protective sleeve (See, for example, U.S. Pat. No. 4,601, 710). Upon removing the trocar from cannula 22, sealing valve 64 closes automatically to preserve the state of insufflation of the body cavity. Pressure exerted by the insufflation gases through cannula 22 biases first member 68 and second member 70 towards each other thereby closing contact region 72.

Sealing valve 64 also prevents escape of gas or other fluids from the body cavity. The user manipulates sealing member 30 to expose cavity 32 for corresponding receipt of an instrument 114 or a scope to be inserted through sealing apparatus 20. Movement of sealing member 30 facilitates the spherical movement of cavity 32 relative to cannula 22. The spherical movement of cavity 32 relative to cannula 22 includes a combination of arcuate manipulation relative to cannula 22, in the direction shown by arrow B, and rotatable manipulation about longitudinal axis A, in the direction shown by arrow C.

Surgical instrument 114 is manipulated in the direction of arrow D. Opening 112 of cap ring 110, cavity 32, passageway 38 and axial lumen 28 each have at least a portion aligned during introduction of surgical instrument 114 therethrough. Upper portion 90 and lower portion 92 of pathway 89 advantageously facilitate spherical movement of cavity 32 of sealing member 30, described above, so that surgical instrument 114 can be introduced through passageway 38 and axial lumen 28 of cannula 22.

During a surgical procedure, the user manipulates surgical instrument 114 within the body cavity facilitated by the corresponding spherical movement of cavity 32. This advantageously facilitates manipulation of surgical instrument 114 into difficult to reach areas within the body cavity at difficult angular orientations. Cavity 32 accommodates various orientations of surgical instrument 114 while maintaining a fluid tight seal with instrument 114 thereby maintaining a fluid tight seal between the body cavity and the outside atmosphere. Instrument 114 is removed from the body cavity and passed through cavity 32. Sealing valve 64 maintains seal integrity between the body cavity and the outside atmosphere.

Figure 4:
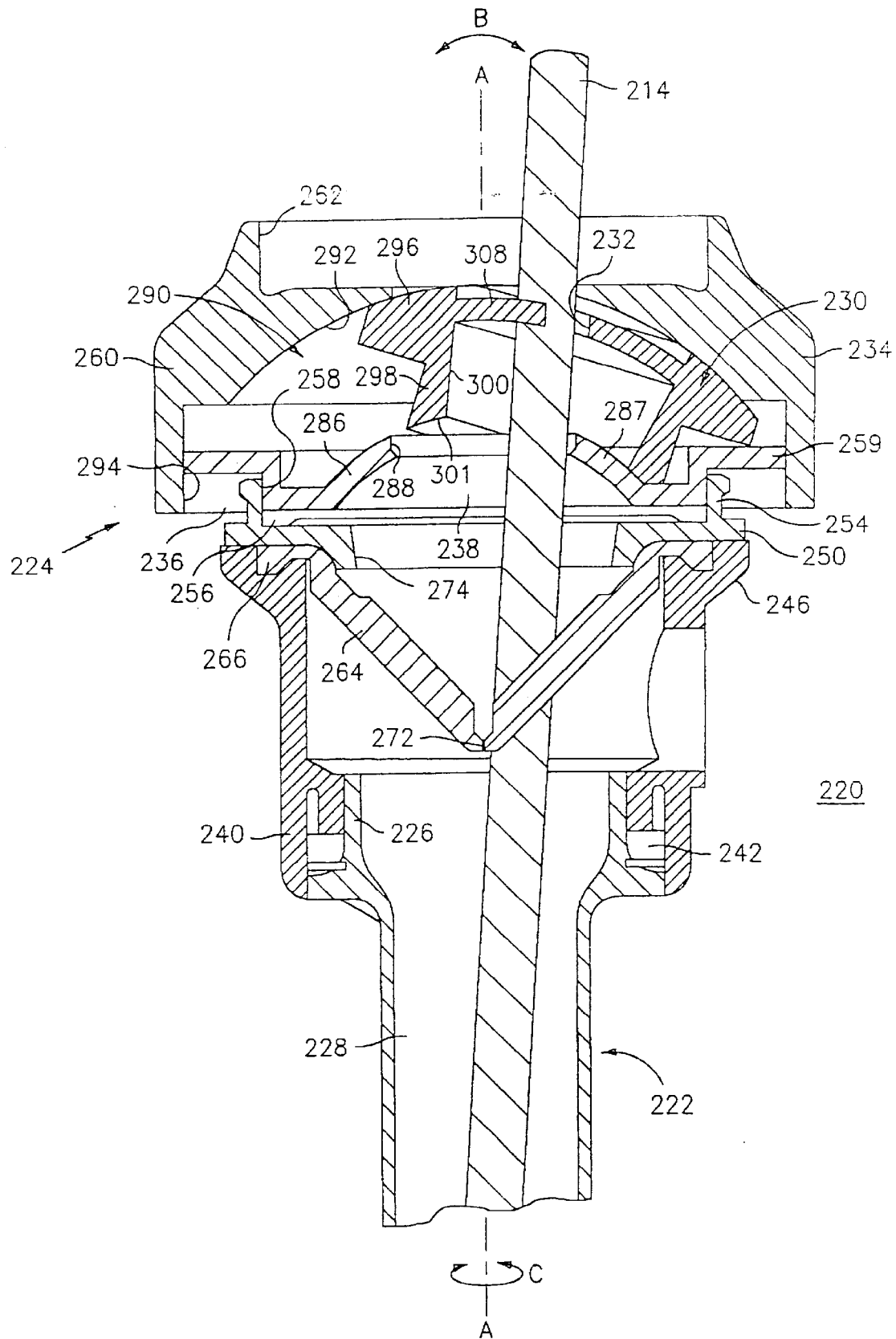
FIG. 4 is a side cross-sectional view of an alternate embodiment of the sealing apparatus, shown in cut-away, and having instrumentation disposed therein.

Referring to FIG. 4, an alternate embodiment of the sealing apparatus is shown, similar to that described with regard to FIGS. 1–3. A sealing apparatus 220 includes a housing 224 mounted to a cannula housing 240, similar to that discussed above. Cannula housing 240 is detachably mounted to a proximal end 226 of a cannula 222. A washer 242 facilitates mounting of cannula housing 240 with cannula 222 by providing support and alignment therebetween. Cannula housing 240 has an exterior surface 246 that is engageable by a user for mounting and manipulation of sealing apparatus 220. Cannula 222 includes an axial lumen 228 and defines a longitudinal axis A. Axial lumen 228 is in fluid communication with a passageway 238 defined by housing 224.

Sealing apparatus 220 has a sealing member 230, similar to that described above, that is moveably disposed within housing 224 and defines a cavity 232 configured for receipt of an instrument 214. Movement of sealing member 230 causes spherical movement of cavity 232 relative to cannula 222 while maintaining a fluid tight seal with instrument 214. Sealing apparatus 220 has relatively moveable components that provide the spherical movement referred to facilitating lateral and vertical movement of cavity 232 relative to cannula 222.

A stabilizing plate 250 is mounted to cannula housing 240 in a sealing engagement. Stabilizing plate 250 includes a flange portion 254 that provides support and alignment of the components of sealing apparatus 220. An annular ring 256 is mounted to stabilizing plate 250 within flange 254 and engages an interior surface 258 thereof. Annular ring 256 provides a buffer between stabilizing plate 250 and the components of sealing apparatus 220. Stabilizing plate 250 includes an opening 274 in communication with passageway 238 and configured for reception and passage of surgical instrument 214.

A sealing valve 264 is disposed within passageway 238 of housing 224. Sealing valve 264 includes a flange portion 266 that is supported on cannula housing 240. Stabilizing plate 250 mounts onto sealing valve 264 and cannula housing 240 for retention of sealing valve 264 within sealing apparatus 220. Sealing valve 264, similar to that described above, defines a contact region 272 for receiving instrument 214.

Flange 254 of stabilizing plate 250 and annular ring 256 are configured for supporting engagement of a sealing element 286. Sealing element 286 is mounted to flange 254 of stabilizing plate 250 and annular ring 256 by threading, adhesives, etc., facilitating support and definition of a moveable pathway 290 of sealing member 230. Sealing element 286 includes a dome portion 287, defining an opening 288 configured for reception and passage of surgical instrument 114, and a flange portion 289. Sealing element 286 supports sealing member 230. Sealing member 230 moves relative to sealing element 286 and forms a substantial seal therewith.

A retainer 260 of housing 224 is mounted to sealing element 286 for support and enclosure of the internal components of sealing apparatus 220. Retainer 260 includes an opening 262 in communication with passageway 238 and configured for reception and passage of surgical instrument 214. Retainer 260 may be appropriately mounted with sealing element 286 by threading, adhesives, bayonet locking, etc., as readily understood by one skilled in the art.

Retainer 260 includes an upper inner surface 292 having a substantially spherical configuration and a lower inner surface 294 having a substantially circular cross-section. Sealing element 286 and inner surfaces 292 and 294 of retainer 260 cooperate to define pathway 290.

Sealing member 230 has a substantially spherical flange 296 and a base 298 that are monolithically formed. It is contemplated that the components of sealing member 230 may be separately fabricated and integrally assembled. Flange 296 moveably engages inner surface 292 of retainer 260. Base portion 298 includes an opening 300 for passage and accommodation of surgical instrumentation. Surface 301 of base portion 298 has a spherical configuration for moveably engaging dome portion 287 of sealing element 286, facilitating spherical movement of sealing member 230 and cavity 232 within pathway 290. Spherical movement of cavity 232 relative to cannula 222 includes arcuate movement relative to cannula 222, in the direction shown by arrows B, and rotation about longitudinal axis A, in the direction shown by arrows C. Flange portion 296 engages inner surface 292 and flange portion 289 of sealing element 286 to define moveable limits of sealing member 230. It is contemplated that engagement of the surgical instrument with housing 224 and/or the cannula assembly when disposed with sealing member 230, may also moveably limit sealing member 230.

Sealing member 230 includes a flexible seal 308 which is monolithically formed with flange 296 and is recessed therein. Flexible seal 308 is a thin annular elastomeric membrane that defines cavity 232 which is configured to receive surgical instrument 214, similar to that described with regard to FIGS. 1–3. Flexible seal 308 is positioned with sealing member 230 such that cavity 232 is spherically moveable relative to cannula 222. The openings, described above, communicating with passageway 238 of sealing apparatus 220 each have at least a portion aligned during introduction of surgical instrument 214 therethrough, similar to that described with regard to FIGS. 1–3. In operation, sealing apparatus 220 accommodates movement and maintains a substantial seal with various surgical instruments during a surgical procedure, similar to that described with regard to FIGS. 1–3.

Figure 5:
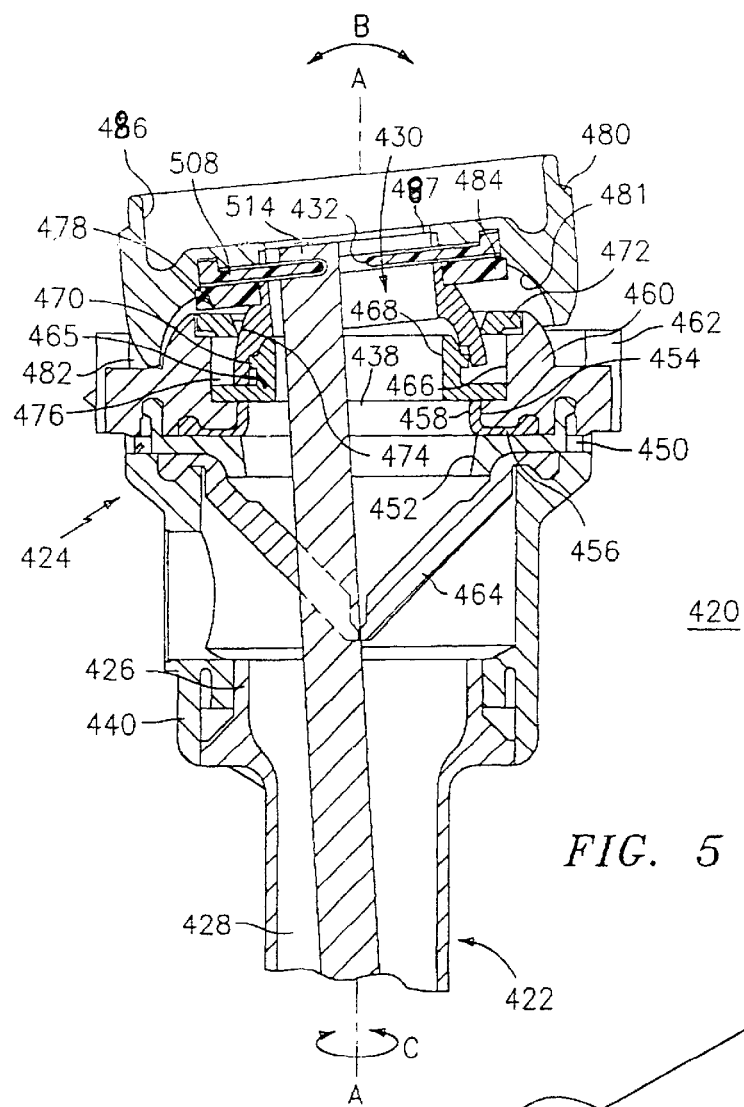
FIG. 5 is a side cross-sectional view of another embodiment of the sealing apparatus, shown in cut-away, having instrumentation disposed therein.
Figure 6:
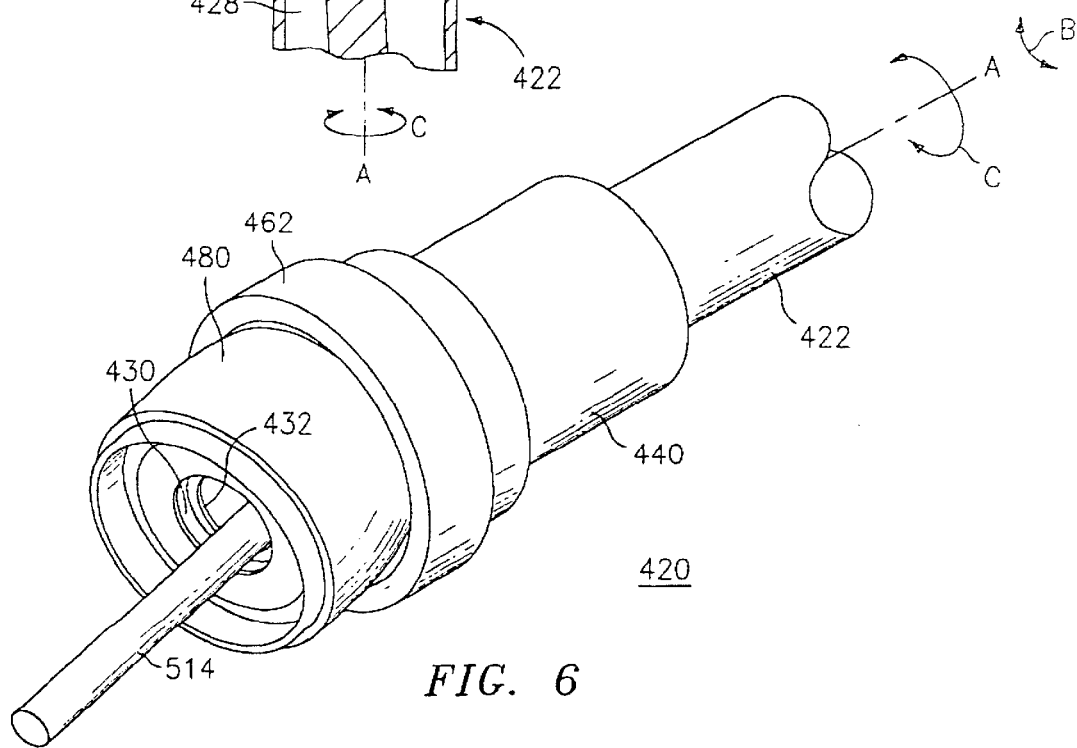
FIG. 6 is a perspective view of the sealing apparatus and the instrumentation shown in FIG. 5.

Referring to FIGS. 5 and 6, another alternate embodiment of the sealing apparatus is shown, similar to those described with regard to FIGS. 1–4. A sealing apparatus 420 includes a housing 424 mounted to a cannula housing 440. Cannula housing 440 is detachably mounted to a proximal end 426 of a cannula 422 having an axial lumen 428 and defining a longitudinal axis A. Axial lumen 428 is in fluid communication with a passageway 438 of housing 424.

Sealing apparatus 420 has a sealing member 430 that is moveably disposed within housing 424 and defines a cavity 432 configured for receipt of an instrument 514. Movement of sealing member 430 causes spherical movement of cavity 432 relative to cannula 422 while maintaining a fluid tight seal with instrument 514. Sealing member 430 is fixedly mounted to a portion of housing 424, such as, for example, a moveable retainer 480, discussed below, such that moveable retainer 480 is correspondingly spherically moveable relative to cannula 422.

A stabilizing plate 450 is mounted to cannula housing 440 in a sealing engagement for support and alignment of the components of sealing apparatus 420. Stabilizing plate 450 includes an opening 452 in communication with passageway 438 and configured for reception and passage of surgical instrument 514. A sealing valve 464, similar to those described with regard to FIGS. 1–4, is disposed within passageway 438 of housing 424. Sealing valve 464 is mounted between stabilizing plate 450 and cannula housing 440 and retained therein forming a seal therewith.

A support 454 is disposed within housing 424 and configured for alignment and support of components of sealing apparatus 420. Support 454 includes a flange portion 456 and an opening 458 which is configured for reception and passage of surgical instrument 514. Flange portion 456 is mounted to stabilizing plate 450.

A stationary retainer 460 of housing 424 is mounted to support 454 for support and alignment thereon. Stationary retainer 460 is also mounted to stabilizing plate 450 for alignment therewith. Stationary retainer 460 includes an exterior surface 462 that is engageable by a user for manipulation of sealing apparatus 420.

A sealing element 465 is mounted onto support 454 and within an opening 466 of stationary retainer 460. Sealing element 465 includes an opening 468 which is in communication with passageway 438 and configured for reception and passage of surgical instrument 514. Sealing element 465 includes step portion 470 and ring portion 472 mounted to stationary retainer 460.

Sealing member 430 is moveably supported by sealing element 465. Sealing element 465 defines a radial opening 474, which is defined by ring portion 472, that permits movement of sealing member 430 therein. Step portion 470 defines a moveable limit of sealing member 430. Sealing element 465 and stationary retainer 460 cooperate to define a first portion 476 of a moveable pathway 478 of sealing member 430.

Sealing member 430 includes a support ring 484 which is integrally assembled therewith and fixedly mounted to a moveable retainer 480 of housing 424. Support ring 484 may be monolithically formed with sealing member 430 or moveable retainer 480. Moveable retainer 480 has an outer opening 486 and an inner opening 487 for passage of surgical instrument 514. An inner surface 481 of moveable retainer 480 has a substantially spherical configuration for moveable engagement with a corresponding spherically shaped portion of stationary retainer 460. Moveable retainer 480 cooperates with stationary retainer 460 to define a second portion 482 of pathway 478.

Support ring 484 is fixedly mounted to moveable retainer 480 such that cavity 432 of sealing member 430 and moveable retainer 480 are correspondingly spherically moveable relative to cannula 422 for accommodating movement of surgical instrument 514 and maintaining a substantially fluid tight seal therewith. Sealing member 430 is spherically moveable within first portion 476. Sealing member 430 is moveable within first portion 476 and step portion 470 of sealing element 465 provides a moveable limit thereof. Moveable retainer 480 is moveable within second portion 482 and stationary retainer 460 provides a moveable limit thereof. Thus, cavity 432 and moveable retainer 480 are correspondingly spherically moveable relative to cannula 422 which includes a combination of arcuate movement relative to cannula 422, in the direction shown by arrows B, and rotatable movement about longitudinal axis A, in the direction shown by arrows C.

Sealing member 430 includes flexible seal 508 which is fixedly mounted to moveable retainer 480. Flexible seal 508 defines cavity 432 and is positioned within sealing member 430 and mounted to moveable retainer 480 such that cavity 432 and moveable retainer 480 are correspondingly spherically moveable relative to cannula 422. The openings, described above, communicating with passageway 438 each have at least a portion aligned during introduction of surgical instrument 514 therethrough, similar to that described with regard to FIGS. 1–4. In operation, sealing apparatus 420 accommodates movement and maintains a substantial seal with various surgical instrumentation during a surgical procedure, similar to that described with regard to FIGS. 1–4.

Figure 7:
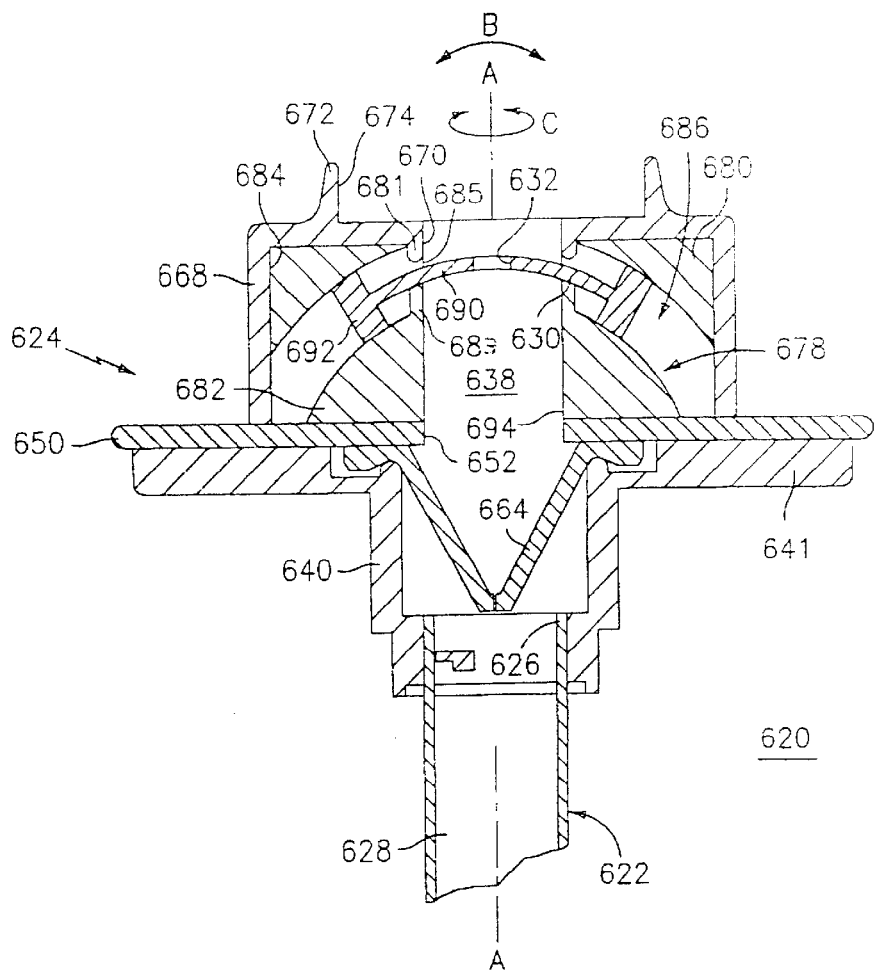
FIG. 7 is a side cross-sectional view of another alternate embodiment of the sealing apparatus, shown in cutaway.
Figure 8:
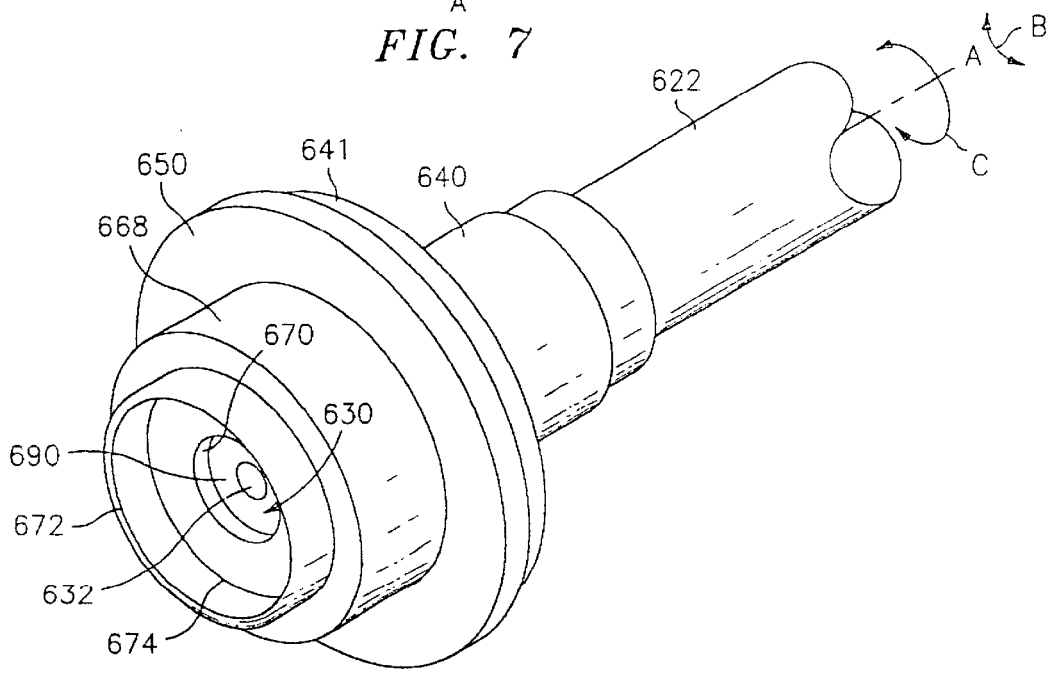
FIG. 8 is a perspective view of the sealing apparatus shown in FIG. 7.

Referring to FIGS. 7 and 8, another embodiment of the sealing apparatus is shown, similar to those described above with regard to FIGS. 1–6. A sealing apparatus 620 includes a housing 624 mounted to a cannula housing 640. Cannula housing 640 is detachably mounted to a proximal end 626 of a cannula 622 having an axial lumen 628 and defining a longitudinal axis A. Axial lumen 628 is in fluid communication with a passageway 638 of housing 624.

Sealing apparatus 620 has a sealing member 630 that is moveably disposed within housing 624 and defines a cavity 632 configured for receipt of a surgical instrument (not shown). Movement of sealing member 630 causes spherical movement of cavity 632 relative to cannula 622 while maintaining a fluid tight seal with the surgical instrument disposed therein.

A stabilizing plate 650 is mounted to a flange 641 of cannula housing 640 in a sealing engagement. Flange 641 has a diameter that provides increased surface area for support and alignment of the components of sealing apparatus 620. This advantageously facilitates improved stability during a surgical procedure. Stabilizing plate 650 includes an opening 652 configured for reception and passage of surgical instruments. A sealing valve 664 is disposed within passageway 638 of housing 624, similar to those described. Sealing valve 664 is mounted and forms a seal between cannula housing 640 and stabilizing plate 650.

A retainer 668 of housing 624 is mounted to stabilizing plate 650 in a coaxial orientation for support and enclosure of the components of sealing apparatus 620. An opening 670 of retainer 668 is in communication with passageway 638 and configured for reception and passage of surgical instruments. Retainer 668 includes a flange 672 which defines a cavity 674 for guiding surgical instruments that are introduced into sealing apparatus 620.

A sealing element 678 includes a first member, such as, for example, an upper portion 680 and second member, such as, for example, a lower portion 682 which are disposed within housing 624. Upper portion 680 is mounted to an inner surface 684 of retainer 668 and lower portion 682 is mounted to stabilizing plate 650. Lower portion 682 defines opening 694 that is configured for reception and passage of surgical instruments. Sealing element 678 may be mounted by adhesives, screws, etc. Upper portion 680 and lower portion 682 cooperate with inner surface 684 of housing 624 and stabilizing plate 650 to define a pathway 686 for movement of sealing member 630. A portion of pathway 686 is disposed between upper portion 680 and lower portion 682. Pathway 686 is a substantially spherically configured cavity that defines a moveable limit of sealing member 630 due to the configuration of portions 680, 682.

Sealing member 630 is moveably supported by sealing element 678. Retainer 668 and lower portion 682 of sealing element 678 have flanges 681 and 683, respectively. Flanges 681 and 683 define a radial opening 685 that facilitates movement of sealing member 630 within pathway 686. Sealing member 630 includes a flexible seal 690 and an end portion, such as, for example, a flange 692. Cavity 632 of sealing member 630 is spherically moveable as facilitated by movement of sealing member 630 through opening 685 and pathway 686. Sealing member 630 is moveably limited as defined by the engagement of flange 692 of sealing member 630 and flanges 681, 683 of retainer 668 and lower portion 682, respectively. Thus, cavity 632 of sealing member 630 is spherically moveable relative to cannula 622 which includes a combination of arcuate movement relative to cannula 622, in the direction shown by arrows B, and rotatable movement about longitudinal axis A, in the direction shown by arrows C.

Flexible seal 690 defines cavity 632 and is positioned with sealing member 630 such that cavity 632 is spherically moveable relative to cannula 622. The openings communicating with passageway 638 each have at least a portion aligned during introduction of surgical instrumentation, similar to that described above. In operation, sealing apparatus 620 accommodates movement and maintains a substantial seal with various surgical instrumentation during a surgical procedure, similar to that described above.

Figure 9:
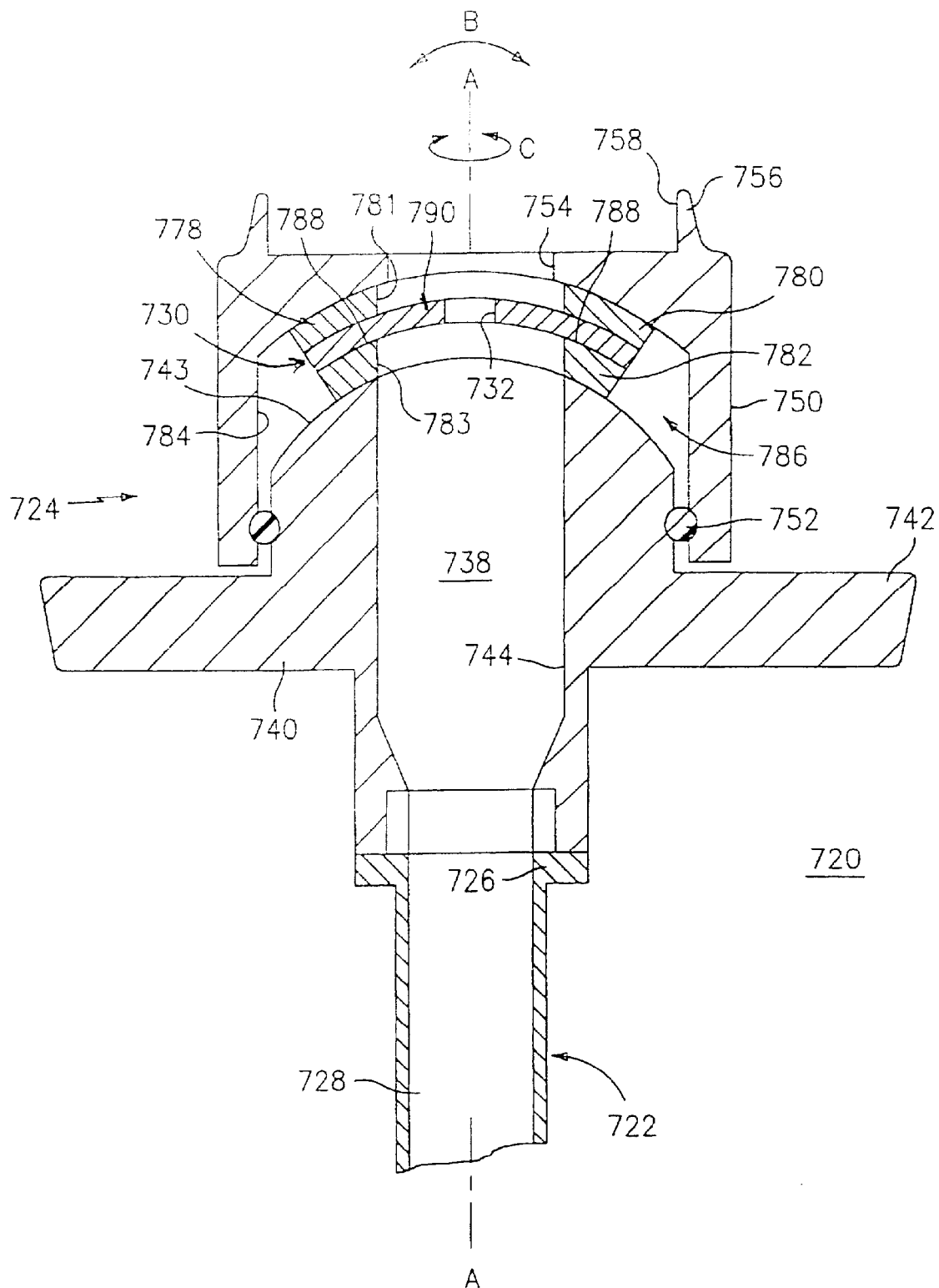
FIG. 9 is a side cross-sectional view of another embodiment of the sealing apparatus, shown in cutaway.

Referring to FIG. 9, another embodiment of the sealing apparatus is shown, similar to those described above with regard to FIGS. 1–8. A sealing apparatus 720 includes a housing 724, having a passageway 738, mounted to a cannula housing 740. Cannula housing 740 is detachably mounted to a proximal end 726 of a cannula 722 having an axial lumen 728 and defining a longitudinal axis A. Sealing apparatus 720 has a sealing member 730 that is moveably disposed within housing 724 and defines a cavity 732 configured for receipt of a surgical instrument (not shown). Movement of sealing member 730 causes spherical movement of cavity 732 relative to cannula 722 while maintaining a fluid tight seal with the surgical instrument disposed therein. Cannula housing 740 includes a flange 742 having an increased diameter, similar to that described with regard to FIGS. 7 and 8. A longitudinal opening 744 forms a portion of passageway 738 and is configured for reception and passage of surgical instrumentation.

A retainer 750 of housing 724 is mounted on cannula housing 740 in a coaxial orientation for support, alignment and enclosure of the components of sealing apparatus 720. Retainer 750 forms a fluid tight seal with cannula housing 740 as facilitated by a sealing gasket 752. It is contemplated that retainer 750 may be directly mounted to cannula housing 740 by, for example, adhesives, clips, etc. An opening 754 of retainer 750 is in communication with passageway 738 and configured for reception and passage of surgical instrumentation. Retainer 750 includes a flange 756 which defines a cavity 758 for guiding surgical instruments to be introduced into sealing apparatus 720.

Sealing member 730 is moveably supported by a sealing element 778 that includes an upper portion 780 and a lower portion 782. Upper portion 780 is mounted to a spherically configured portion of an inner surface 784 of retainer 750 and lower portion 782 is mounted to a spherically configured portion 743 of cannula housing 740. Upper portion 780 and lower portion 782 define openings 781 and 783, respectively, which are in coaxial alignment with opening 754 of retainer 750 and opening 744 of cannula housing 740. It is envisioned that openings 781, 783 may be axially offset with openings 754, 744. Sealing element 778 is fabricated from a rigid material and mounted by adhesives, screws, etc. Sealing element 778 may also be formed from other materials such as, non-rigid, elastic, etc.

Upper portion 780, lower portion 782, inner surface 784 of retainer 750 and surface 743 of cannula housing 740 cooperate to define a pathway 786 for movement of sealing member 730. A portion of pathway 786 is disposed between upper portion 780 and lower portion 782. Pathway 786 is a spherically configured cavity that moveably limits sealing member 730 at inner surface 784. Upper portion 780 and lower portion 782 define an opening 788 therebetween that facilitates movement of sealing member 730 within pathway 786.

Sealing member 730 includes a flexible seal 790 that defines cavity 732. Cavity 732 is spherically moveable relative to cannula 722 which includes a combination of arcuate movement, in the direction shown by arrows B, and rotatable movement about longitudinal axis A, in the direction shown by arrows C. Thus, cavity 732 is spherically moveable relative to cannula 622. The openings communicating with passageway 738 each have at least a portion aligned during introduction of surgical instrumentation, similar to that described above. In operation, sealing apparatus 720 accommodates movement and maintains a substantial seal with various surgical instrumentation during a surgical procedure, similar to that described above.

Figure 10:
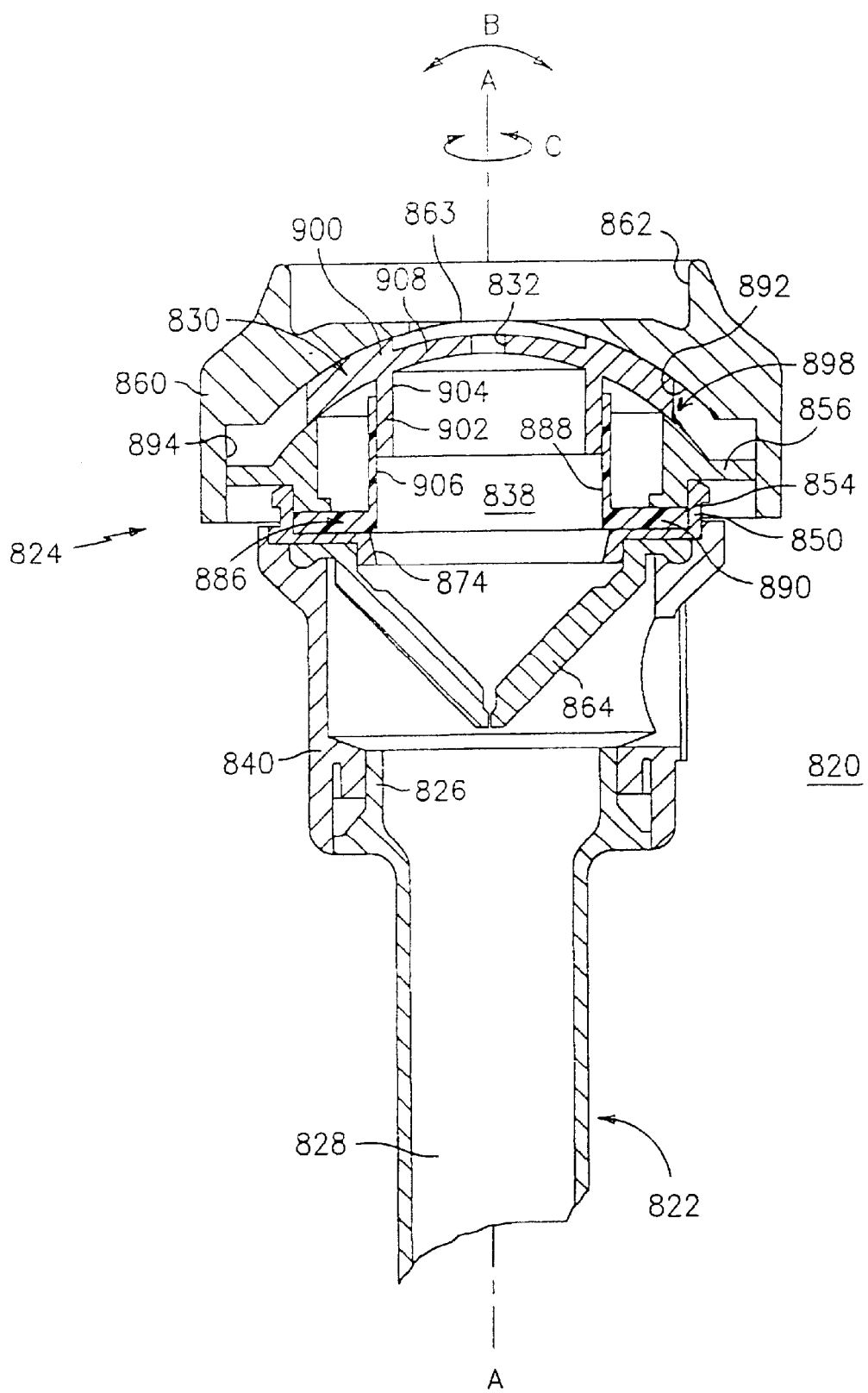
FIG. 10 is a side cross-sectional view of another embodiment of the sealing apparatus, shown in cut-away.

Referring to FIG. 10, another embodiment of the sealing apparatus is shown, similar to those described above. A sealing apparatus 820 includes a housing 824, having a passageway 838, mounted to a cannula housing 840. Cannula housing 840 is detachably mounted to a proximal end 826 of a cannula 822 having an axial lumen 828 and defining a longitudinal axis A. Sealing apparatus 820 has a sealing member 830 that is moveably disposed within housing 824 and defines a cavity 832 configured for receipt of a surgical instrument (not shown). Movement of sealing member 830 causes spherical movement of cavity 832 relative to cannula 822, as facilitated by a flexible sealing element, discussed below, while maintaining a fluid tight seal with the surgical instrument.

A stabilizing plate 850 is mounted to cannula housing 840 in a sealing engagement. Stabilizing plate 850 includes a flange portion 854 that provides support and alignment of the components of sealing apparatus 820. Stabilizing plate 850 includes an opening 874 in communication with passageway 838 and configured for reception and passage of surgical instrumentation. A sealing valve 864 is mounted within passageway 838 of housing 824, similar to those described above. Stabilizing plate 850 is configured for support of a sealing element 886. Sealing element 886 is configured as a flexible boot and defines an opening 888 configured for reception and passage of surgical instrumentation. Sealing element 886 can be fabricated from elastomeric materials, such as, for example, rubber, etc. Sealing element 886 is mounted to stabilizing plate 850 within flange 854 by adhesives, etc. A support 856 is mounted on to a flange 890 of sealing element 886 and engages flange portion 854 of stabilizing plate 850 facilitating alignment of the components of sealing apparatus 820.

A retainer 860 of housing 824 is mounted to support 856 for support and enclosure of the internal components of sealing apparatus 820. Retainer 860 includes openings 862, 863 in communication with passageway 838 and configured for guided reception and passage of surgical instrumentation. Retainer 860 includes an upper inner surface 892 having a spherical configuration and a lower inner surface 894 having a substantially circular cross-section. Sealing element 886 and inner surfaces 892 and 894 of retainer 860 cooperate to define a pathway 898 of sealing member 830.

Sealing member 830 has a spherical flange 900 and a base 902 that are monolithically formed. The parts of sealing member 830 may be integrally assembled. Base 902 is mounted to a resilient portion 906 of sealing element 886 by adhesives, etc. Base 902 may also be monolithically formed with sealing element 886. Base 902 includes an opening 904 for passage and accommodation of surgical instrumentation. Spherical flange 900 engages surface 892 of retainer 860 facilitating spherical movement of sealing member 830 within passageway 898.

Sealing element 886 includes resilient portion 906 configured to facilitate movement of sealing member 830 within pathway 898. Resilient portion 906 biases sealing member 830 to a centered position relative to longitudinal axis A of cannula 822 and in substantially coaxial alignment therewith. Alternatively, sealing element 886 may be mounted with housing 824 such that resilient portion 906 biases sealing member 830 in an offset orientation relative to longitudinal axis A. It is envisioned that resilient portion 906 may be disposed with housing 824 at an angular orientation relative to longitudinal axis A.

Engagement of flange 900 of sealing member 830 with support 856 and inner surface 894 of retainer 860 provides a moveable limit for sealing member 830. Thus, cavity 832 of sealing member 830, as facilitated by sealing element 886, is spherically moveable relative to cannula 822 which includes a combination of arcuate movement relative to cannula 822, in the direction shown by arrows B, and rotatable movement about longitudinal axis A, in the direction shown by arrows C.

Sealing member 830 includes flexible seal 908 that defines cavity 832 and is positioned with sealing member 830 such that cavity 832 is spherically moveable relative to cannula 822, discussed above. The openings communicating with passageway 838 each have at least a portion aligned during introduction of surgical instrumentation. In operation, sealing apparatus 820 accommodates movement of and maintains a substantial seal with various surgical instrumentation during a surgical procedure, similar to that described above.

Figure 11:
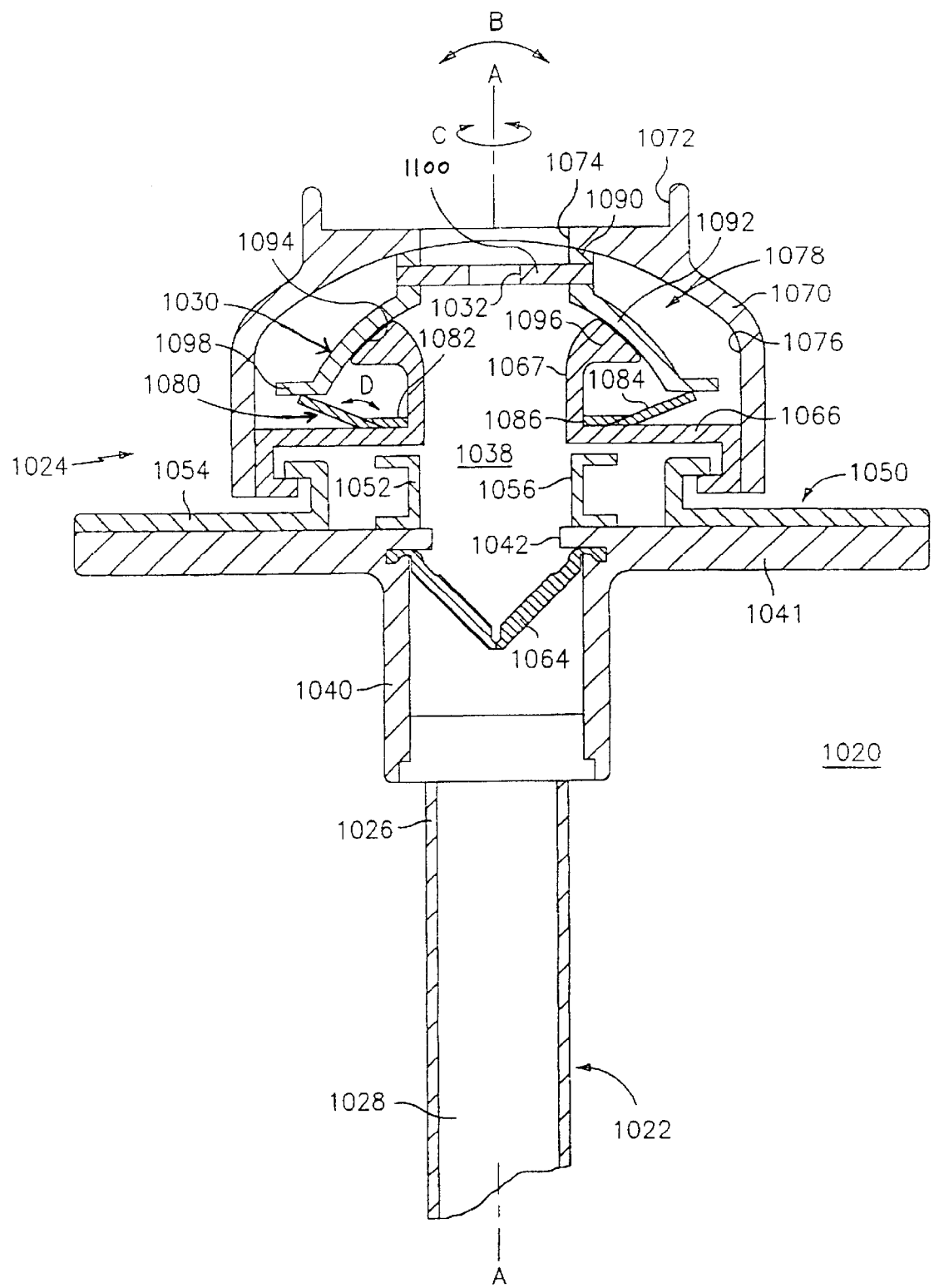
FIG. 11 is a side cross-sectional view of another embodiment of the sealing apparatus, shown in cut-away.

Referring to FIG. 11, another embodiment of the sealing apparatus is shown, similar to those described above. A sealing apparatus 1020 includes a housing 1024, having a passageway 1038, which is mounted to a cannula housing 1040 having an opening 1042 configured for reception and passage of surgical instrumentation. Cannula housing 1040 is detachably mounted to a proximal end 1026 of a cannula 1022 having an axial lumen 1028 and defining a longitudinal axis A. Sealing apparatus 1020 has a sealing member 1030 that is moveably disposed within housing 1024 and defines a cavity 1032 configured for receipt of a surgical instrument (not shown). Movement of sealing member 1030 causes spherical movement of cavity 1032 relative to cannula 1022, as facilitated by a flexible sealing element, discussed below, while maintaining a fluid tight seal with the surgical instrument.

A stabilizing plate 1050 is mounted to a flange 1041 of cannula housing 1040 in a sealing engagement. Stabilizing plate 1050 includes an inner ring 1052 and an outer flange 1054 which may be monolithically formed, integrally assembled or separately mounted with sealing apparatus 1020. Stabilizing plate 1050 includes an opening 1056 in communication with passageway 1038 and configured for reception and passage of surgical instrumentation. A sealing valve 1064 is mounted within passageway 1038 of housing 1024.

A support 1066 is mounted to outer flange 1054 of stabilizing plate 1050 for support and alignment of the components of sealing apparatus 1020. A retainer 1070 of housing 1024 is mounted to support 1066 for support and enclosure of the internal components of sealing apparatus 1020. Retainer 1070 includes openings 1072 and 1074 which are in communication with passageway 1038 and configured for guided reception of surgical instrumentation. Retainer 1070 includes an inner surface 1076 which cooperates with support 1066 to define a pathway 1078 of sealing member 1030.

Sealing member 1030 has a collar portion 1090 and a bell portion 1092. The components of sealing member 1030 are monolithically formed, but may, however, be integrally assembled. Collar portion 1090 of sealing member 1030 engages inner surface 1076 of retainer 1070 facilitating spherical movement of sealing member 1030 relative to inner surface 1076. Bell portion 1092 has a spherically configured inner surface 1094 which engages a corresponding spherically shaped portion 1096 of support 1066 for movement relative thereto. Bell portion 1092 includes a flange 1098 mounted to a sealing element 1080 by adhesives, etc. It is contemplated that flange 1098 may be monolithically formed with sealing element 1080.

Sealing element 1080 is fabricated from an elastomeric material and includes a base portion 1082 and a flange portion 1084. Base portion 1082 is mounted to support 1066 and includes an opening 1086 for disposal of support 1066 therein. Flange portion 1098 of sealing member 1030 is mounted to flange 1084. It is envisioned that flange 1098 and flange 1084 may be independently moveable. It is contemplated that flange 1098 may be monolithically formed with sealing element 1080.

Sealing element 1080 is substantially circular and resilient such that during operation, manipulation of surgical instrumentation disposed within sealing member 1030 causes movement thereof and a pressure to be exerted on sealing element 1080. This causes flange portion 1084 to flex relative to base portion 1082, in the direction shown by arrows D. Spherical movement of sealing member 1030 is advantageously facilitated within pathway 1078 while accommodating movement of and maintaining a fluid tight seal with surgical instrumentation disposed therein.

A surgical instrument can be manipulated with sealing member 1030 such that the resilient quality of sealing element 1080 facilitates movement of sealing member 1030 within pathway 1078 and biases sealing member 1030 to a centered position relative to longitudinal axis A of cannula 1022 and in substantially coaxial alignment therewith, similar to that described with regard to FIG. 10. Engagement of flange 1098 of sealing member 1030 with support 1066 provides a moveable limit for sealing member 1030. Mounting of flange 1098 to flange 1084 may also provide a moveable limit of sealing member 1030.

Thus, cavity 1032 of sealing member 1030, as facilitated by sealing element 1080, is spherically moveable relative to cannula 1022 which includes a combination of arcuate movement relative to cannula 1022, in the direction shown by arrows B, and rotatable movement about longitudinal axis A, in the direction shown by arrows C. Sealing member 1030 defines a flexible seal 1100 and is positioned within collar portion 1090 of sealing member 1030 such that cavity 1032 is spherically moveable relative to cannula 1022, discussed above. In operation, sealing apparatus 1020 accommodates movement of and maintains a substantial seal with various surgical instrumentation during a surgical procedure, similar to that described above.

Figure 12:
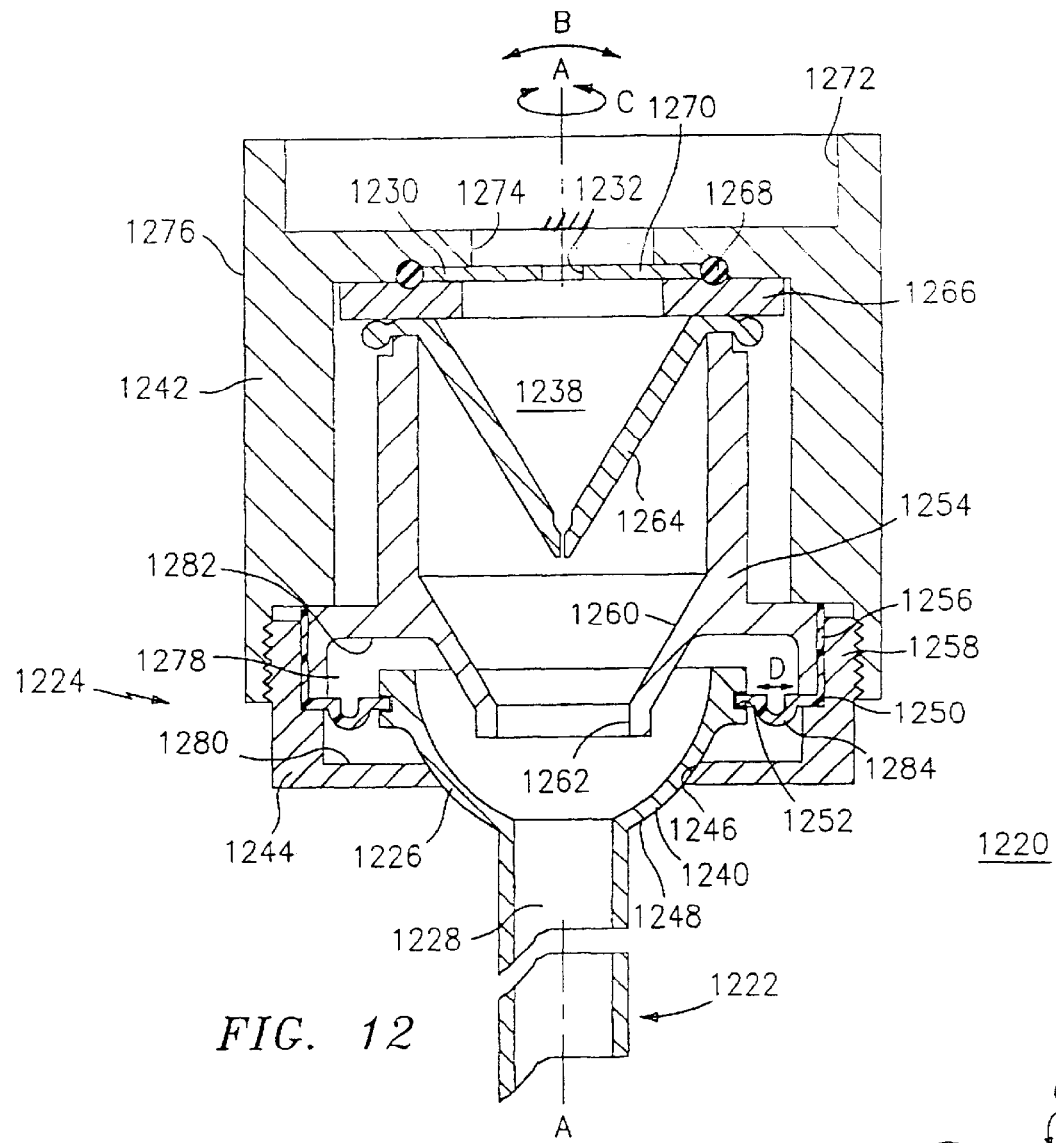
FIG. 12 is a side cross-sectional view of another embodiment of the sealing apparatus, shown in cut-away.
Figure 13:
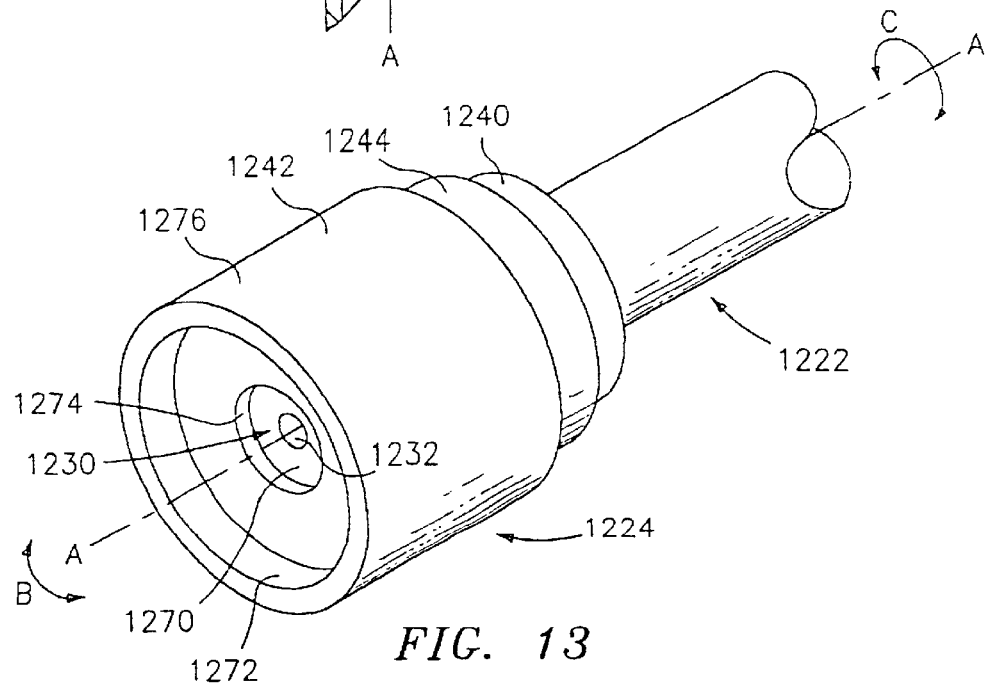
FIG. 13 is a perspective view of the sealing apparatus shown in FIG. 12.

Referring to FIGS. 12 and 13, another embodiment of the sealing apparatus is shown, similar to those described above. A sealing apparatus 1220 includes a housing 1224 which is detachably mounted to a cannula head 1240 formed adjacent a proximal end 1226 of a cannula 1222. Cannula 1222 has an axial lumen 1228, defines a longitudinal axis A and is in fluid communication with a passageway 1238 of housing 1224.

Sealing apparatus 1220 has a sealing member 1230, similar to those described above, that is fixedly mounted within housing 1224 and defines a cavity 1232 configured for receipt of a surgical instrument. Movement of sealing member 1230 causes corresponding spherical movement of housing 1224 relative to cannula 1222 while maintaining a fluid tight seal with a surgical instrument (not shown), as will be discussed in greater detail hereinbelow. Movement of sealing member 1230 may be caused, for example, by manipulation of surgical instrumentation disposed therein. It is contemplated that housing 1224 may independently accommodate instrumentation and may be independently moveable relative to cannula 1222. Independent movement of housing 1224 may be caused by, for example, manipulation of the housing. Sealing apparatus 1220 has relatively moveable components that provide the spherical movement referred to facilitating lateral and vertical movement of housing 1224 relative to cannula 1222.

Housing 1224 includes an upper housing 1242 and a lower housing 1244. Lower housing 1244 includes an opening 1246 configured to accommodate and engage a corresponding spherically shaped surface 1248 of cannula head 1240. This configuration facilitates spherical movement of housing 1224 relative to cannula 1222. Lower housing 1244 is mounted to cannula head 1240 by a cannula seal gasket 1250. Cannula seal gasket 1250 is fabricated from an elastomeric material and engages a slot 1252 of cannula head 1240 in a sealing engagement. A support 1254 abuts a cylindrical portion 1256 of seal gasket 1250 against lower housing 1244 for support and alignment of the components of sealing apparatus 1220.

Upper housing 1242 mounts onto support 1254 and is threaded to a threaded portion 1258 of lower housing 1244 for support and enclosure of the internal components of sealing apparatus 1220. It is contemplated that upper housing 1242 may also be mounted to lower housing 1244 by, such as, for example, welding, snap connection, bayonet locking, etc. Support 1254 includes an inner surface 1260 having a conical configuration for guided reception and accommodation of surgical instrumentation. An opening 1262 of support 1254 is moveably disposed within cannula head 1240 and spherically moveable with housing 1224 relative to cannula 1222. A sealing valve 1264 is disposed within passageway 1238 of housing 1224. Sealing valve 1264 is mounted onto support 1254 and a seal clamp 1266 fixes sealing valve 1264 therebetween, within sealing apparatus 1220.

Sealing member 1230 is mounted in a sealing engagement between upper housing 1242 and seal clamp 1266, as facilitated by gaskets 1268. Sealing member 1230 includes a flexible seal 1270 that defines cavity 1232 and is positioned with sealing member 1230 such that cavity 1232 is correspondingly spherically moveable with housing 1224 relative to cannula 1222.

Upper housing 1242 includes openings 1272, 1274 for guided reception and passage of surgical instrumentation therethrough. Upper housing 1242 includes an outer surface 1276 for manipulation of sealing apparatus 1220. Outer surface 1276 is manipulated causing corresponding spherical movement of housing 1224 relative to cannula 1222 as facilitated by the configuration and engagement of surface 1248 of cannula head 1240 and opening 1246 of lower housing 1244.

Spherical movement of housing 1224 facilitates motion of cannula head 1240 within a pathway 1278. Pathway 1278 is cooperatively defined by an inner surface 1280 of lower housing 1244 and a bottom surface 1282 of support 1254. Cannula seal gasket 1250 compensates for relative movement between housing 1224 and cannula head 1240 by a resilient bend 1284 which flexibly moves outwardly and inwardly, in the direction of arrows D, corresponding to the spherical motion of housing 1224 relative to cannula 1222. Housing 1224 is moveably limited in the range defined by the engagement of cannula head 1240 with bottom surface 1282 of support 1254 and inner surface 1280 of lower housing 1244. It is contemplated that seal gasket 1250 may moveably limit housing 1224.

Thus, housing 1224 and cavity 1232 of sealing member 1230 are correspondingly spherically moveable relative to cannula 1222 which includes a combination of arcuate movement relative to cannula 1222, in the direction shown by arrows B, and rotatable movement about longitudinal axis A, in the direction shown by arrows C. The openings communicating with passageway 1238 each have at least a portion aligned during introduction of surgical instrumentation. In operation, scaling apparatus 1220 accommodates movement and maintains a substantial seal with various surgical instrumentation during a surgical procedure, similar to that described above.

Figure 14:
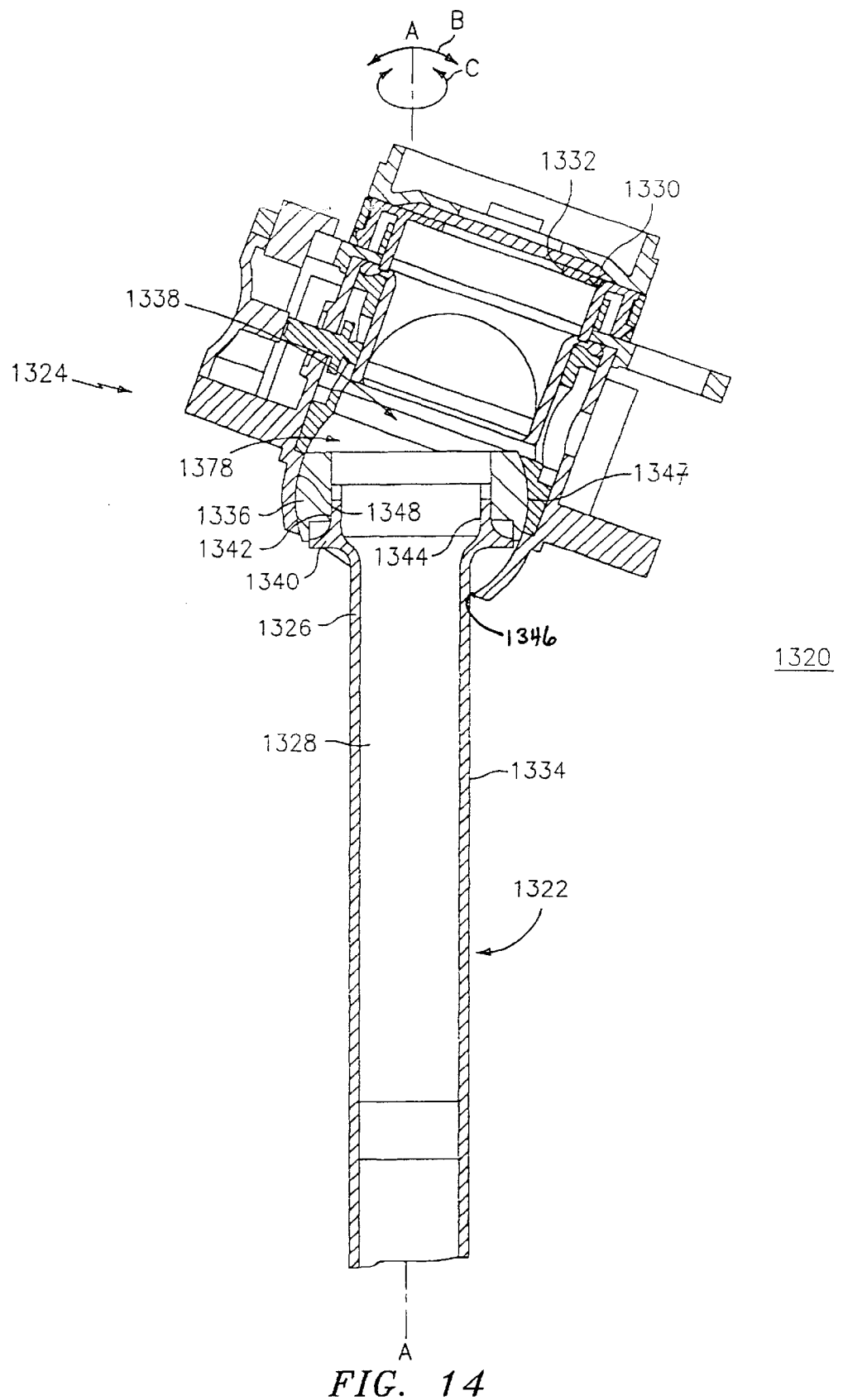
FIG. 14 is a side cross-sectional view of another embodiment of the sealing apparatus, shown in cutaway, having instrumentation disposed therein.

Referring to FIG. 14, an alternate embodiment of the sealing apparatus illustrated in FIGS. 12 and 13 is shown. A sealing apparatus 1320 includes a housing 1324 which is detachably mounted to a cannula head 1340 formed adjacent a proximal end 1326 of a cannula 1322. Cannula 1322 has an axial lumen 1328, defines a longitudinal axis A and is in fluid communication with a passageway 1338 of housing 1324. Sealing apparatus 1320 has a sealing member 1330, similar to those described above, and defines a cavity 1332. Movement of sealing member 1330 causes corresponding spherical movement of housing 1324 relative to cannula 1322 while maintaining a fluid tight seal with a surgical instrument (not shown), similar to that described with regard to FIGS. 12 and 13.

Housing 1324 includes an opening 1346 configured to accommodate and engage an outer surface 1334 of cannula 1322. Housing 1324 is mounted to cannula head 1340 by a mounting ring 1336. Mounting ring 1336 is positioned onto an outer surface 1342 of cannula head 1340 by adhesives, friction fit, etc., and a sealing engagement formed therebetween. Mounting ring 1336 may also include a sealing gasket or the like to facilitate sealing engagement with cannula 1322. An opening 1344 of cannula head 1340 is disposed within housing 1324 such that housing 1324 is moveable relative thereabout and configured for reception and accommodation of surgical instrumentation therein.

Mounting ring 1336 has a spherically configured outer surface 1347 which engages a correspondingly spherically shaped inner surface 1348 of housing 1324. Manipulation of housing 1324 causes corresponding spherical movement of housing 1324 relative to cannula 1322 as facilitated by the configuration and engagement of surface 1347 of mounting ring 1336 and surface 1348 of housing 1324.

Spherical movement of housing 1324 facilitates relative motion of cannula head 1340 within a pathway 1378. Pathway 1378 is cooperatively defined by inner surface 1348 of housing 1324 and cannula 1322. Housing 1324 is moveably limited in the range defined by the engagement of housing 1324 with outer surface 1334 of cannula 1322. It is contemplated that engagement of a surgical instrument with housing 1324 may also provide a moveable limit. Thus, housing 1324 and cavity 1332 of scaling member 1330 are correspondingly spherically moveable relative to cannula 1322 which includes a combination of arcuate movement relative to cannula 1322, in the direction shown by arrows B, and rotatable movement about longitudinal axis A, in the direction shown by arrows C. In operation, sealing apparatus 1320 accommodates movement and maintains a substantial seal with various surgical instrumentation during a surgical procedure, similar to that described above.

Figure 15:
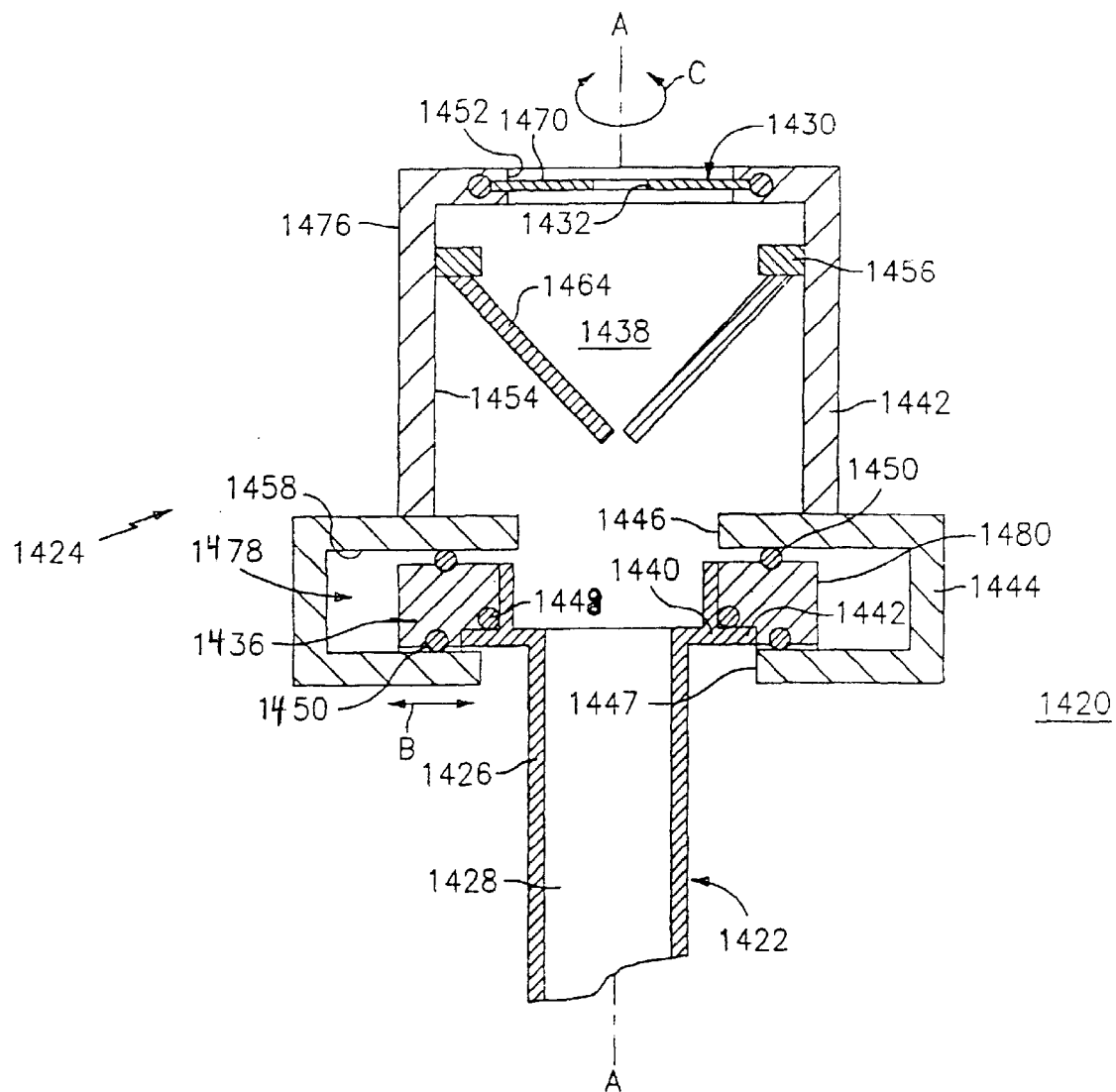
FIG. 15 is a side cross-sectional view of another embodiment of the sealing apparatus, shown in cut-away.

Referring to FIG. 15, yet another embodiment of the sealing apparatus is shown, similar to those described above. A sealing apparatus 1420 includes a housing 1424 which is detachably mounted to a cannula head 1440 formed adjacent a proximal end 1426 of a cannula 1422. Cannula 1422 has an axial lumen 1428, defines a longitudinal axis A and is in fluid communication with a passageway 1438 of housing 1424.

Sealing apparatus 1420 has a sealing member 1430, similar to those described above, that is fixedly mounted with housing 1424 and defines a cavity 1432 configured for receipt of a surgical instrument. Movement of sealing member 1430 causes corresponding lateral movement of housing 1424 relative to longitudinal axis A of cannula 1422 while maintaining a fluid tight seal with a surgical instrument (not shown). It is contemplated that housing 1424 may independently accommodate instrumentation and may be independently moveable relative to longitudinal axis A of cannula 1422. Sealing apparatus 1420 has relatively moveable components that provide the lateral movement referred to.

Housing 1424 includes an upper housing 1442 and a lower housing 1444. Lower housing 1444 includes an opening 1446, configured for reception of surgical instrumentation, and opening 1447, configured for accommodation of lateral movement relative to longitudinal axis A of cannula 1422. A mounting ring 1436 is mounted onto a flange portion 1442 of cannula head 1440 in a sealing engagement. A gasket 1448 facilitates sealing engagement between mounting ring 1436 and flange 1442. Lower housing 1444 is slidably mounted to mounting ring 1436. Sealing gaskets 1450 facilitate slidable movement of lower housing 1444 relative to mounting ring 1436. A sealing engagement is formed between lower housing 1444 and mounting ring 1436 to preserve the atmospheric integrity of the surgical procedure from gas and/or fluid leakage between the body cavity and the outside atmosphere.

A sealing valve 1464 is disposed within passageway 1438 of housing 1424. Sealing valve 1464 is mounted to an inner surface 1454 of upper housing 1442 via a support ring 1456 by adhesives, etc. Upper housing 1442 mounts onto lower housing 1444 for enclosure of the internal components of sealing apparatus 1420. Upper housing 1442 includes an opening 1452 having sealing member 1430 disposed therein.

Sealing member 1430 is mounted to upper housing 1442 in a sealing engagement within opening 1452. Sealing member 1430 includes a flexible seal 1470 that defines cavity 1432 and is positioned within opening 1452 such that cavity 1432 is correspondingly laterally moveable with housing 1424 relative to longitudinal axis A of cannula 1422. It is contemplated that sealing member 1430 may be monolithically formed with upper housing 1442.

Housing 1424 includes an outer surface 1476 for manipulation of sealing apparatus 1420. Outer surface 1476 is manipulated causing corresponding lateral movement of housing 1424 relative to cannula 1422 as facilitated by the configuration and engagement of an inner surface 1458 of lower housing 1444 and gaskets 1450. Lateral movement of housing 1424 facilitates relative motion of cannula head 1440 within a pathway 1478 of housing 1424. Pathway 1478 is cooperatively defined by inner surface 1458 of lower housing 1444, an outer surface 1480 of mounting ring 1436 and cannula head 1440.

Housing 1424 is moveably limited in the range defined by the engagement of opening 1447 of lower housing 1444 and cannula 1422. It is contemplated that moveable limits may be provided by engagement of mounting ring 1436 and lower housing 1444 and/or engagement of a surgical instrument with housing 1424. Thus, housing 1424 and cavity 1432 of sealing member 1430 are correspondingly laterally moveable relative to cannula 1422, in the direction shown by arrows B. Housing 1424 and cavity 1432 are also rotatably moveable about longitudinal axis A, in the direction shown by arrows C. In operation, sealing apparatus 1420 accommodates movement and maintains a substantial seal with various surgical instrumentation during a surgical procedure, similar to that described above.

It will be understood that various modifications may be made to the embodiments disclosed herein. Therefore, the above description should not be construed as limiting, but merely as exemplifications of the various embodiments. Those skilled in the art will envision other modifications within the scope and spirit of the claims appended hereto.

What is claimed:

1. A sealing apparatus comprising:
    a housing being mountable to an elongate shaft including an axial lumen, the housing defining an arcuate pathway therein and having proximal and distal ends; and
    a sealing member defining a cavity for receiving an object in sealing relation therewith and having at least a portion thereof disposed within the housing, the sealing member adapted to traverse the arcuate pathway of the housing about an axis of curvature upon offset manipulation of an object therein, the axis of curvature being disposed distally of the sealing member.

2. A sealing apparatus according to claim 1, wherein the elongate shaft includes a cannula assembly having a cannula and a cannula housing, said cannula being detachably mountable to the cannula housing so as to form at least one substantial seal.

3. A sealing apparatus according to claim 1, wherein the sealing member has a substantially parabolic cross-section.

4. A sealing apparatus according to claim 1, wherein the cavity is configured for receiving and forming a substantial seal with an instrument.

5. A sealing apparatus according to claim 1, further comprising a sealing valve having at least a portion thereof being disposed within a passageway defined by the housing, the passageway being in fluid communication with the axial lumen of the elongate shaft and the sealing valve being configured to form a substantial seal with an instrument.

6. A sealing apparatus according to claim 5, wherein the sealing valve includes a first member and a second member being inwardly biased so as to form the substantial seal with the instrument.

7. A sealing apparatus according to claim 6, wherein the first and second members define a contact region configured for receiving and forming the substantial seal with the instrument.

8. A sealing apparatus according to claim 5, wherein at least a portion of the sealing valve comprises a flexible membrane.

9. A sealing apparatus according to claim 1, wherein the housing defines a passageway communicating with the cavity of the sealing member and the axial lumen of the elongate shaft.

10. A sealing apparatus according to claim 1, wherein the arcuate pathway includes a first portion and a second portion.

11. A sealing apparatus according to claim 1, wherein the sealing member includes an end portion defining a moveable limit of the sealing member within the arcuate pathway.

12. A sealing apparatus according to claim 1, wherein the sealing member includes at least one biasing member configured for engaging an inner surface of the housing so as to bias the sealing member to a centered position relative to the housing.

13. A sealing apparatus according to claim 12, wherein the sealing member includes a plurality of biasing members.

14. A sealing apparatus, which comprises:
    a housing being mountable to an elongate shaft including an axial lumen;
    a sealing member defining a cavity and having at least a portion thereof disposed within the housing, the sealing member being spherically moveable relative to the elongate shaft; and
    a sealing element mounted to the housing and being configured for moveably supporting and forming a substantial seal with the sealing member during movement thereof, the sealing element having a resilient portion being configured to bias the cavity of the sealing member in general alignment with a longitudinal axis of the elongate shaft upon off axis manipulation of an object positioned within the sealing member.

15. A sealing apparatus according to claim 14, wherein the sealing member is biased to a centered position relative to the longitudinal axis and in substantially coaxial alignment therewith.

16. A sealing apparatus comprising:
    a housing having a proximal and a distal portion, the housing being detachably mountable to a cannula assembly including a cannula housing and a cannula, the cannula having an axial lumen and defining a longitudinal axis, the housing including a passageway in communication with the axial lumen of the cannula;
    an elastomeric sealing member defining a cavity configured for receipt of and forming a substantial seal with an instrument, the sealing member being movably disposed within a pathway of the housing, the sealing member having a spherically shaped cross-section such that the cavity of the sealing member is spherically moveable relative to the cannula, the sealing member further including a plurality of biasing members radially extending therefrom and being configured to engage an inner surface of the housing so as to bias the sealing member to a centered position relative to the housing; and
    an annular sealing element being mounted to the housing, the annular sealing element defining a cavity and including a flange, the sealing member being movably supported on the flange and forming a substantial seal therewith, wherein at least a portion of the cavity defined by the sealing element is capable of substantial alignment with at least a portion of the cavity of the sealing member.

17. A sealing apparatus according to claim 16, further comprising a sealing valve having at least a portion thereof being disposed within the passageway of the housing, the sealing valve being configured to form a substantial seal.

18. A seal assembly for use with an access device, which comprises:
    a seal housing having a passageway extending therethrough for reception of an object and defining a longitudinal axis, and proximal and distal ends; and
    a sealing member disposed within the seal housing, the sealing member defining an opening to permit passage of the object in substantial sealed relation therewith, the sealing member adapted to move within the seal housing along at least two axes of movement in response to movement of the object relative to the seal housing, one of the axes being a pivotal axis which is distally displaced of the sealing member whereby the sealing member pivots about the pivotal axis.

19. A seal assembly according to claim 18, further including a sealing element mounted within the seal housing, the sealing element slidably engageable with the sealing member during movement of the sealing member within the seal housing, the sealing element adapted to form a substantial fluid-tight seal with the sealing member.

20. A seal assembly according to claim 19 wherein the sealing member includes a proximal section and a distal general bell-shaped section, the bell-shaped section defining an internal surface engageable with the sealing element.

21. A seal assembly according to claim 20 wherein the proximal section includes a resilient seal, the resilient seal defining the opening of the sealing member.

22. A seal assembly according to claim 18 including a biasing member, the biasing member configured and dimensioned to bias the sealing member toward a position wherein the opening of the sealing member is in substantial alignment with the axis of the seal housing.

23. A seal assembly according to claim 22 wherein the biasing member is connected to the sealing member.

24. A seal assembly according to claim 18 wherein the seal housing includes an internal arcuate cavity, the arcuate cavity defining an arcuate path of movement.

25. A seal assembly according to claim 24 including a resilient seal disposed within the internal arcuate cavity of the seal housing.

26. A seal assembly according to claim 25 wherein the resilient seal defines an outer flange and an inner seal portion, the outer flange engageable with internal surfaces defining the internal arcuate cavity of the seal housing in substantial sealed relation therewith.

27. A seal assembly according to claim 18, wherein a second of the axes is a rotational axis whereby the sealing member is rotatable about the rotational axis.

28. A seal assembly for use with an access device, which comprises:

a seal housing having a passageway extending therethrough for reception of an object and defining a longitudinal axis;

a seal mount disposed within the seal housing, the seal mount including an object seal defining an opening to permit passage of the object in substantial sealed relation therewith, the seal mount adapted to move within the seal housing about an arcuate path of movement in response to movement of the object relative to the seal housing; and a biasing member extending radially outwardly relative to the longitudinal axis from an outer surface of the seal mount, the biasing member configured and dimensioned to bias the seal mount wherein the opening of the seal is in substantial alignment with the axis of the seal housing.

29. The seal assembly according to claim 28, wherein the seal mount is adapted to pivot about a first axis of movement and rotate about a second axis of movement within the seal housing.

30. The seal assembly according to claim 29 wherein the first axis is distally displaced from the object seal.

31. The seal assembly according to claim 28 including a plurality of the biasing members extending from an outer radial wall of the seal housing and engageable with an internal wall surface of the seal housing.

32. The seal assembly according to claim 28 wherein the biasing member is adapted to engage an inner wall surface of the seal housing upon offset manipulation of the object relative to the longitudinal axis and thereby bias the seal mount and the opening of the seal in substantial alignment with the longitudinal axis of the seal housing.

33. A seal assembly for use with an access device, which comprises:

a seal housing having a passageway extending therethrough for reception of an object and defining a longitudinal axis; and an object seal disposed within the seal housing, the object seal defining an opening to permit passage of the object in substantial sealed relation therewith, the object seal adapted to move within the seal housing about at least two axes of movement, a first of the axes being a pivotal axis extending transverse to the longitudinal axis of the seal housing and distal of the object seal, and a second of the axes being a rotation axis extending in general parallel relation with the longitudinal axis of the seal housing.

* * * * *